United States Patent
Ottosen

(10) Patent No.: US 6,541,670 B2
(45) Date of Patent: Apr. 1, 2003

(54) AMINOBENZOPHENONES AS INHIBITORS OF IL 1β AND TNF-α

(75) Inventor: Erik Rytter Ottosen, Ølstykke (DK)

(73) Assignee: Leo Pharmaceutical Products Ltd. A/S, Ballerup (DK)

( * ) Notice: Subject to any disclaimer, the term of this patent is extended or adjusted under 35 U.S.C. 154(b) by 0 days.

(21) Appl. No.: 09/787,532

(22) PCT Filed: Nov. 29, 2000

(86) PCT No.: PCT/DK00/00653
§ 371 (c)(1),
(2), (4) Date: Mar. 20, 2001

(87) PCT Pub. No.: WO01/42189
PCT Pub. Date: Jun. 14, 2001

(65) Prior Publication Data
US 2003/0013770 A1 Jan. 16, 2003

Related U.S. Application Data
(60) Provisional application No. 60/169,333, filed on Dec. 6, 1999.

(51) Int. Cl.$^7$ .................. C07C 211/00; C07C 249/00; C07C 251/00; C07C 259/00; C07C 291/00; C07C 255/00
(52) U.S. Cl. .............. 564/432; 564/431; 564/266; 564/253; 558/411; 558/412; 558/415; 558/418; 558/422
(58) Field of Search .................. 564/1, 305, 123, 564/307, 315, 321, 431, 432, 161, 162, 163, 166, 167, 168, 169, 170, 171, 253, 259, 265, 266; 558/303, 411, 412, 414, 415, 418, 422

(56) References Cited
FOREIGN PATENT DOCUMENTS
JP     81-61259     10/1982
WO    WO 98/32730   * 7/1998

OTHER PUBLICATIONS
Bhavsar et al. Man–Made textiles in India, 29(5), pp. 224–230 (1986).*
Hussein et al, Iraqi J. Sci., 22(1):54–66 (1981).
Bhavsar et al, Man–Made Textiles in India, 30(6):275–6 (1987).
Bhavsar et al, Man–Made Textiles In India, 29(5):224–308 (1986).
Bhavsar et al, Man–Made Textiles in India, 28(1):425, 427–9, 431 (1985).
* cited by examiner Primary Examiner—Johann Richter
Assistant Examiner—Elvis O. Price
(74) Attorney, Agent, or Firm—Birch, Stewart, Kolasch & Birch, LLP

(57) ABSTRACT

A compound of the general formula I

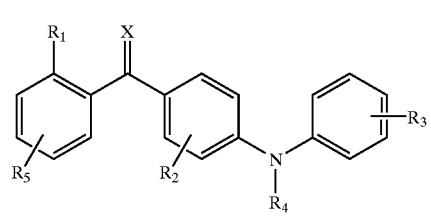

wherein
$R_1$ represents a substituent selected from the group consisting of halogen, hydroxy, mercapto, trifluoromethyl, amino, $(C_1-C_3)$alkyl, $(C_2-C_3)$olefinic group, $(C_1-C_3)$alkoxy, $(C_1-C_3)$alkylthio, $(C_1-C_6)$alkylamino, $(C_1-C_3)$alkoxycarbonyl, cyano, —$CONH_2$, phenyl, and nitro;
$R_2$ represents one or more, same or different substituents selected from the group consisting of hydrogen, halogen, hydroxy, mercapto, trifluoromethyl, amino, $(C_1-C_3)$alkyl, $(C_2-C_3)$olefinic group, $(C_1-C_3)$alkoxy, $(C_1-C_3)$alkylthio, $(C_1-C_6)$alkylamino, $(C_1-C_3)$alkoxycarbonyl, cyano, —$CONH_2$, phenyl, and nitro;
$R_3$ represents one or more, same or different substituents selected from the group consisting of hydrogen, halogen, hydroxy, mercapto, trifluoromethyl, cyano, carboxy, carbamoyl, $(C_1-C_{10})$alkyl, $(C_2-C_{10})$olefinic group, $(C_3-C_8)$monocyclic hydrocarbon group, $(C_1-C_{10})$alkoxy, $(C_1-C_{10})$alkylthio, $(C_1-C_{10})$alkoxycarbonyl, and phenyl;
$R_4$ represents hydrogen, $(C_1-C_6)$alkyl, $(C_2-C_6)$olefinic group, or $(C_3-C_6)$monocyclic hydrocarbon group;
$R_5$ represents one or more, same or different substituents selected from the group consisting of hydrogen and $R_1$;
X represents oxygen, sulphur, or N—OH;
and salts thereof with pharmaceutically acceptable acids, hydrates and solvates, may be used in the prophylaxis or treatment of inflammatory diseases.

31 Claims, No Drawings

AMINOBENZOPHENONES AS INHIBITORS OF IL 1β AND TNF-α

This application is the national phase of international application PCT/DK00/00653 filed Nov. 29, 2000 which designated the U.S.

This application also claims the benefit of U.S. Provisional Application No. 60/169,333, filed Dec. 6, 1999.

FIELD OF THE INVENTION

This invention relates to a hitherto unknown class of compounds which shows anti-inflammatory effects, to pharmaceutical preparations containing these compounds, to dosage units of such preparations, and to their use in the treatment and prophylaxis of asthma and allergy; inflammatory diseases, such as arthritis, including rheumatoid arthritis and spondyloarthritis, gout, atherosclerosis, chronic inflammatory bowel disease (Crohn's disease), uveitis, septic shock, and AIDS; proliferative and inflammatory skin disorders, such as psoriasis, atopic dermatitis, and acne; and osteoporosis.

BACKGROUND OF THE INVENTION

Previously, a series of closely related aminobenzophenones (e.g. 4-(2-amino-4-nitrophenylamino)benzophenone) have been described (Hussein, F. A. et al, Iraqi J. Sci., 22, 54–66 (1981)). However, there is no description of their uses. WO 98/32730 discloses aminobenzophenone inhibitors of interleukin 1β (IL-1β) and tumour necrosis factor α (TNF-α) secretion in vitro, said compounds being potentially useful for treatment of inflammatory diseases in which the production of cytokines is involved in the pathogenesis, e.g. asthma, rheumatoid arthritis, psoriasis, contact dermatitis, and atopic dermatitis. Furthermore the compounds of PCT/DK98/00008 were tested in vivo for anti-inflammatory properties in the 12-O-tetradecanoylphorbol-13-acetate (TPA) induced murine chronic skin inflammation model, (De Young, L. M. et al., Agents Actions, 26, 335–341 (1989); Carlson, R. P. et al., Agents Actions, 17, 197–204 (1985); Alford, J. G. et al., Agents Action, 37, (1992); Stanley, P. L. et al., Skin Pharmacol, 4, 262–271 (1991)). In this chronic skin inflammation model the compounds had the same potency compared to the reference compound hydrocortisone.

The purpose of the present invention is to provide further pharmacologically active benzophenone derivatives and related compounds.

It has surprisingly been found that novel aminobenzophenone derivatives according to the general formula I are potent inhibitors of interleukin 1β (IL-1β) and tumour necrosis factor α (TNF-α) secretion in vitro, making them potentially useful for treatment of inflammatory diseases, in which the secretion and regulation of cytokines or more specifically interleukin 1β (IL-1β) and tumour necrosis factor α (TNF-α) are involved in the pathogenesis. The inhibition or down regulation of the cytokines is possibly due to an inhibition of MAP kinases. The preparation of structurally related aminobenzophenones useful as dyes for textiles is disclosed in Man-Made Text. India (1987), 30(6), 275–6; Man-Made Text. India (1986), 29(5), 224–30; and Man-Made Text. India (1985), 28(11), 425, 427–9, 431; an related aminobenzophenone is disclosed in JP 81-61259 as a reactant in the preparation of fluoran color formers.

SUMMARY OF THE INVENTION

The compounds of the present invention are represented by the general formula I

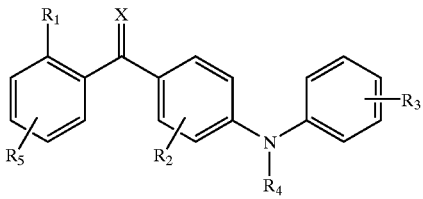

wherein $R_1$ represents a substituent selected from the group consisting of halogen, hydroxy, mercapto, trifluoromethyl, amino, $(C_1-C_3)$alkyl, $(C_2-C_3)$olefinic group, $(C_1-C_3)$ alkoxy, $(C_1-C_3)$alkylthio, $(C_1-C_6)$alkylamino, $(C_1-C_3)$ alkoxycarbonyl, cyano, —$CONH_2$, phenyl, or nitro;

$R_2$ represents one or more, same or different substituents selected from the group consisting of hydrogen, halogen, hydroxy, mercapto, trifluoromethyl, amino, $(C_1-C_3)$alkyl, $(C_2-C_3)$olefinic group, $(C_1-C_3)$alkoxy, $(C_1-C_3)$alkylthio, $(C_1-C_6)$alkylamino, $(C_1-C_3)$ alkoxycarbonyl, cyano, —$CONH_2$, phenyl, or nitro;

$R_3$ represents one or more, same or different substituents selected from the group consisting of hydrogen, halogen, hydroxy, mercapto, trifluoromethyl, cyano, carboxy, carbamoyl, $(C_1-C_{10})$alkyl, $(C_2-C_{10})$olefinic group, $(C_3-C_8)$monocyclic hydrocarbon group, $(C_1-C_{10})$alkoxy, $(C_1-C_{10})$alkylthio, $(C_1-C_{10})$ alkoxycarbonyl, or phenyl;

$R_4$ represents hydrogen, $(C_1-C_6)$alkyl, $(C_2-C_6)$olefinic group, or $(C_3-C_6)$monocyclic hydrocarbon group;

$R_5$ represents one or more, same or different substituents selected from the group consisting of hydrogen and $R_1$;

X represents oxygen, sulphur, or N—OH;

with the proviso that when X represents oxygen then $R_1$, $R_2$ and $R_5$ together does not represent more than 8 fluorine substituents and with the proviso that the following compounds are not included in formula I:

2-Chloro-4'-(2-chlorophenylamino)benzophenone,
2-Chloro-4'-(phenylamino)benzophenone,
2-Hydroxy-4'-(phenylamino)benzophenone,
2-Hydroxy-4'-(4-hydroxyphenylamino)benzophenone,
2-Hydroxy-4'-(4-methoxyphenylamino)benzophenone,
2-Hydroxy-4'-(2-hydroxyphenylamino)benzophenone,
2-Hydroxy-4'-(2-methoxyphenylamino)benzophenone,
2-Methoxy-4'-(2-methoxyphenylamino)benzophenone, and
2-Methyl-4'-(4-methoxyphenylamino)benzophenone.

DETAILED DESCRIPTION OF THE INVENTION

Preferred embodiments of the invention

In compounds of formula I $R_1$ preferably represents a substituent selected from the group consisting of fluoro, chloro, bromo, hydroxy, trifluoromethyl, amino, $(C_1-C_2)$ alkyl, $(C_2-C_3)$alkenyl, $(C_1-C_3)$alkoxy, $(C_1-C_3)$ alkoxycarbonyl, cyano, and —$CONH_2$;

$R_2$ represents one or more, same or different substituents selected from the group consisting of hydrogen, fluoro, chloro, bromo, hydroxy, trifluoromethyl, amino, $(C_1-C_3)$ alkyl, $(C_2-C_3)$alkenyl, and $(C_1-C_3)$alkoxy.

$R_3$ represents one or more, same or different substituents selected from the group consisting of hydrogen, fluoro, chloro, bromo, hydroxy, trifluoromethyl, $(C_1-C_6)$alkyl, $(C_2-C_6)$alkenyl, $(C_1-C_6)$alkoxy, $(C_1-C_6)$alkoxycarbonyl, cyano, carboxy, and —$CONH_2$.

R$_4$ represents hydrogen, (C$_1$–C$_4$)alkyl, or (C$_2$–C$_4$)olefinic group;

X represents oxygen or sulphur;

R$_5$ represents one or more, same or different substituents selected from the group consisting of hydrogen, fluoro, chloro, bromo, hydroxy, trifluoromethyl, amino, (C$_1$–C$_2$) alkyl, (C$_2$–C$_3$)alkenyl, (C$_1$–C$_3$)alkoxy, (C$_1$–C$_3$) alkoxycarbonyl, cyano, and —CONH$_2$;

More preferably R$_1$ represents a substituent selected from the group consisting of fluoro, chloro, bromo, hydroxy, methyl, and methoxy;

R$_2$ represents one or more, same or different substituents selected from the group consisting of hydrogen, fluoro, chloro, bromo, hydroxy, methyl, and methoxy;

R$_3$ represents one or more, same or different substituents selected from the group consisting of hydrogen, fluoro, chloro, bromo, hydroxy, methyl, methoxy, cyano, and carboxy;

R$_4$ represents hydrogen, methyl, or ethyl;

R$_5$ represents one or more, same or different substituents selected from the group consisting of hydrogen, fluoro, chloro, bromo, hydroxy, trifluoromethyl, methyl, ethyl, and methoxy;

X represents oxygen;

The phenyl group of R$_1$, R$_2$, R$_3$, and R$_5$ may optionally be substituted, e.g. with hydroxy; amino; nitro; cyano; halogen, preferably fluoro, chloro, or bromo; methyl; or methoxy.

A preferred embodiment of the invention is the formula VII:

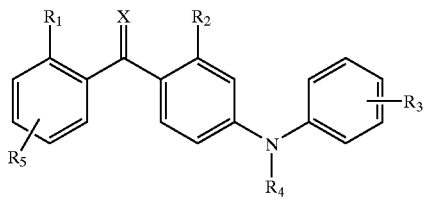

VII wherein X, R$_1$, R$_2$, R$_3$, R$_4$, and R$_5$ have the meanings specified above except that R$_2$ does not represent hydrogen. Preferred compounds of formula VII are compounds wherein R$_2$ represents a halogen atom, preferably chlorine.

Specific compounds of formula I or VII of the invention are:

2-[[3-Chloro-4-(2-methylbenzoyl)]phenylamino] benzonitrile (Compound 101),

2-Chloro-2'-methyl-4-(2-methyl-phenylamino) benzophenone (Compound 102),

2-Chloro-2'-methyl-4-(phenylamino)benzophenone (Compound 103),

2-Chloro-4-(2-methoxy-phenylamino)-2'-methylbenzophenone (Compound 104),

2-Chloro-4-(2-fluoro-phenylamino)-2'-methylbenzophenone (Compound 105),

2-Chloro-4-(2-chloro-phenylamino)-2'-methylbenzophenone (Compound 106), 4-(2-tert-Butyoxy-phenylamino)-2-chloro-2'-methylbenzophenone (Compound 107), 2-Chloro-4-(2-hydroxy-phenylamino)-2'-methylbenzophen- one (Compound 108), 2-Chloro-4-(3-chloro-phenylamino)-2'-methylbenzophenone (Compound 109), 2-Chloro-4-(2-[1,1,1-trifluoromethyl]-phenylamino)-2'-methylbenzophenone (Compound 110), 4-(4-Bromo-2,5-difluoro-phenylamino)-2-chloro-2'-methylbenzophenone (Compound 111), 2-Chloro-4-(2-ethyl-phenylamino)-2'-methylbenzophenone (Compound 112), 2-Chloro-4-(3-[1,1,1-trifluoromethyl]phenylamino)-2'-methylbenzophenone (Compound 113), 2-Chloro-2'-methyl-4-(2-phenyl-phenylamino) benzophenone (Compound 114), 2-Chloro-2'-methyl-4-(3-phenyl-phenylamino) benzophenone (Compound 115), 2-Chloro-4-(4-fluoro-2-methyl-phenylamino)-2'-methylbenzophenone (Compound 116), 2-Chloro-2'-methyl-4-(3-methyl-phenylamino) benzophenone (Compound 117), 2-Chloro-4-(3-methoxy-phenylamino)-2'-methylbenzophenone (Compound 118), 2-Chloro-4-(4-chloro-phenylamino)-2'-methylbenzophenone (Compound 119), 2-Chloro-2'-methyl-4-(4-phenyl-phenylamino) benzophenone (Compound 120), 4-(4-Bromo-phenylamino)-2-chloro-2'-methylbenzophenone (Compound 121), 4-(4-Bromo-3-fluoro-phenylamino)-2-chloro-2'-methylbenzophenone (Compound 122), 4-(2-Bromo-phenylamino)-2-chloro-2'-methylbenzophenone (Compound 123), 2-Chloro-4-(4-chloro-2-methyl-phenylamino)-2'-methylbenzophenone (Compound 124), 2-Chloro-4-(4-chloro-3-fluoro-phenylamino)-2'-methylbenzophenone (Compound 125), 2-Chloro-4-(3-fluoro-phenylamino)-2'-methylbenzophenone (Compound 126), 2-Chloro-4-(3,5-difluoro-phenylamino)-2'-methylbenzophenone (Compound 127), 4-(3-Bromo-phenylamino)-2-chloro-2'-methylbenzophenone (Compound 128), 2-Chloro-4-(3,4-difluoro-phenylamino)-2'-methylbenzophenone (Compound 129), 2-Chloro-4-(5-fluoro-2-methyl-phenylamino)-2'-methylbenzophenone (Compound 130), 2-Chloro-4-(3-fluoro-2-methyl-phenylamino)-2'-methylbenzophenone (Compound 131), Ethyl 2-[[3-chloro-4-(2-methylbenzoyl)]phenylamino] benzoate (Compound 132), 2-Chloro-3'-fluoro-4(4fluoro-2-methyl-phenylamino)-2'-methylbenzophenone (Compound 133), 2-[[3-Chloro-4-(2-methylbenzoyl)]phenylamino]benzoic acid (Compound 134), 2-Chloro-4-(4-fluoro-2-methyl-phenylamino)-2'-methylbenzophenone (Compound 135), 4-(4-Bromo-2-methyl-phenylamino)-2-chloro-2'-methylbenzophenone (Compound 136), 4-(4-Bromo-2-chloro-phenylamino)-2-chloro-2'-methylbenzophenone (Compound 137), 4-(4-Bromo-2-methyl-phenylamino)-2-chloro-4'-methoxy-2'-methylbenzophenone (Compound 138), 4-(4-Bromo-2-methyl-phenylamino)-2,4'-dichloro-2'-methylbenzophenone (Compound 139), 4-(4-Bromo-2-methyl-phenylamino)-2-chloro-4'-fluoro-2'-methylbenzophenone (Compound 140), 4-(4-Bromo-2-methyl-phenylamino)-2-fluoro-2'-methylbenzophenone (Compound 141), 4-(4-Bromo-2-methyl-phenylamino)-2-chloro--2',5'-dimethyl-benzophenone (Compound 142), 2-Chloro-4-(4-cyano-2-methyl-phenylamino)-2'-methylbenzophenone (Compound 143), 4-(4-Bromo-2-methyl-N-ethyl-phenylamino)-2-chloro-2'-methylbenzophenone (Compound 144), 2-Chloro-4-(4-bromo-2-methyl-phenylamino)-4'-ethoxy-2'-methylbenzophenone (Compound 145),
2,3'-Dichloro-4-(4-bromo-2-methyl-phenylamino)-2'-methylbenzophenone (Compound 146), and salts thereof with pharmaceutically acceptable acids, hydrates and solvates.

Compounds of formula Ia wherein X=S and wherein $R_1$, $R_2$, $R_3$, $R_4$, and $R_5$ have the meanings specified for formula I, and compounds of formula Ib wherein X=N—OH and wherein $R_1$, $R_2$, $R_3$, $R_4$, and $R_5$ have the meanings specified for formula I are also generally preferred

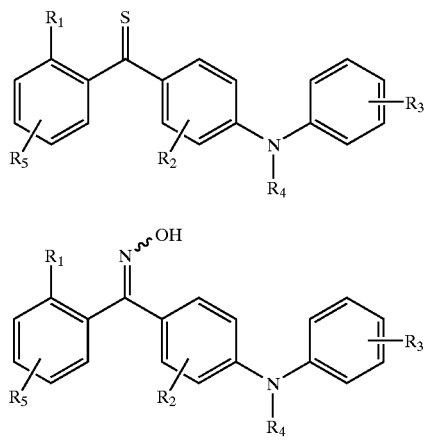

Specific compounds of formula Ia are:

2-[[3-Chloro-4-(2-methyl(thiobenzoyl))]phenylamino] benzonitrile (Compound 301),
2-Chloro-2'-methyl-4-(2-methyl-phenylamino) (thiobenzophenone) (Compound 302),
2-Chloro-2'-methyl-4-(phenylamino)(thiobenzophenone) (Compound 303),
2-Chloro-4-(2-methoxy-phenylamino)-2'-methyl (thiobenzophenone) (Compound 304),
2-Chloro-4-(2-fluoro-phenylamino)-2'-methyl (thiobenzophenone) (Compound 305),
2-Chloro-4-(2-chloro-phenylamino)-2'-methyl (thiobenzophenone) (Compound 306),
4-(2-tert-Butyoxy-phenylamino)-2-chloro-2'-methyl (thiobenzophenone) (Compound 307),
2-Chloro-4-(2-hydroxy-phenylamino)-2'-methyl (thiobenzophenone) (Compound 308),
2-Chloro-4-(3-chloro-phenylamino)-2'-methyl (thiobenzophenone) (Compound 309),
2-Chloro-4-(2-[1,1,1-trifluoromethyl]-phenylamino)-2'-methyl(thiobenzophenone) (Compound 310),
4-(4-Bromo-2,5-difluoro-phenylamino)-2-chloro-2'-methyl (thiobenzophenone) (Compound 311),
2-Chloro-4-(2-ethyl-phenylamino)-2'-methyl (thiobenzophenone) (Compound 312),
2-Chloro-4-(3-[1,1,1-trifluoromethyl]phenylamino)-2'-methyl(thiobenzophenone) (Compound 313),
2-Chloro-2'-methyl-4-(2-phenyl-phenylamino) (thiobenzophenone) (Compound 314),
2-Chloro-2'-methyl-4-(3-phenyl-phenylamino) (thiobenzophenone) (Compound 315),
2-Chloro-4-(4-fluoro-2-methyl-phenylamino)-2'-methyl (thiobenzophenone) (Compound 316),
2-Chloro-2'-methyl-4-(3-methyl-phenylamino) (thiobenzophenone) (Compound 317),
2-Chloro-4-(3-methoxy-phenylamino)-2'-methyl (thiobenzophenone) (Compound 318),
2-Chloro-4-(4-chloro-phenylamino)-2'-methyl (thiobenzophenone) (Compound 319),
2-Chloro-2'-methyl-4-(4-phenyl-phenylamino) (thiobenzophenone) (Compound 320),
4-(4-Bromo-phenylamino)-2-chloro-2'-methyl (thiobenzophenone) (Compound 321),
4-(4-Bromo-3-fluoro-phenylamino)-2-chloro-2'-methyl (thiobenzophenone) (Compound 322),
4-(2-Bromo-phenylamino)-2-chloro-2'-methyl (thiobenzophenone) (Compound 323),
2-Chloro-4-(4-chloro-2-methyl-phenylamino)-2'-methyl (thiobenzophenone) (Compound 324),
2-Chloro-4-(4-chloro-3-fluoro-phenylamino)-2'-methyl (thiobenzophenone) (Compound 325),
2-Chloro-4-(3-fluoro-phenylamino)-2'-methyl (thiobenzophenone) (Compound 326),
2-Chloro-4-(3,5-difluoro-phenylamino)-2'-methyl (thiobenzophenone) (Compound 327),
4-(3-Bromo-phenylamino)-2-chloro-2'-methyl (thiobenzophenone) (Compound 328),
2-Chloro-4-(3,4-difluoro-phenylamino)-2'-methyl (thiobenzophenone) (Compound 329),
2-Chloro-4-(5-fluoro-2-methyl-phenylamino)-2'-methyl (thiobenzophenone) (Compound 330),
2-Chloro-4-(3-fluoro-2-methyl-phenylamino)-2'-methyl (thiobenzophenone) (Compound 331),
Ethyl 2-[[3-chloro-4-(2-methyl(thiobenzoyl))]phenylamino] benzoate (Compound 332),
2-Chloro-3'-fluoro-4-(4-fluoro-2-methyl-phenylamino)-2'-methyl(thiobenzophenone) (Compound 333),
2-[[3-Chloro-4-(2-methyl(thiobenzoyl))]phenylamino] benzoic acid (Compound 334),
2-Chloro-4-(4-fluoro-2-methyl-N-methyl-phenylamino)-2'-methyl(thiobenzophenone) (Compound 335),
4-(4-Bromo-2-methyl-phenylamino)-2-chloro-2'-methyl (thiobenzophenone) (Compound 336),
4-(4-Bromo-2-chloro-phenylamino)-2-chloro-2'-methyl (thiobenzophenone) (Compound 337),
4-(4-Bromo-2-methyl-phenylamino)-2-chloro-4'-methoxy-2'-methyl(thiobenzophenone) (Compound 338),
4-(4-Bromo-2-methyl-phenylamino)-2,4'-dichloro-2'-methyl(thiobenzophenone) (Compound 339),
4-(4-Bromo-2-methyl-phenylamino)-2-chloro-4'-fluoro-2'-methyl(thiobenzophenone) (Compound 340),
4-(4-Bromo-2-methyl-phenylamino)-2-fluoro-2'-methyl (thiobenzophenone) (Compound 341),
4-(4-Bromo-2-methyl-phenylamino)-2-chloro--2',5'-dimethyl-(thiobenzophenone) (Compound 342),
2-Chloro-4-(4-cyano-2-methyl-phenylamino)-2'-methyl (thiobenzophenone) (Compound 343),
4-(4-Bromo-2-methyl-N-ethyl-phenylamino)-2-chloro-2'-methyl(thiobenzophenone) (Compound 344),
2-Chloro-4-(4-bromo-2-methyl-phenylamino)-4'-ethoxy-2'-methyl(thiobenzophenone) (Compound 345),
2,3'-Dichloro-4-(4-bromo-2-methyl-phenylamino)-2'-methyl(thiobenzophenone) (Compound 346), and salts thereof with pharmaceutically acceptable acids, hydrates and solvates.

Specific compounds of formula Ib are:

2-[[3-Chloro-4-[(hydroxyimino)(2-methylphenyl)methyl]] phenylamino]benzonitrile (Compound 401),
2-Chloro-2'-methyl-4-(2-methyl-phenylamino) benzophenone oxime (Compound 402), 2-Chloro-2'-methyl-4-(phenylamino)benzophenone oxime (Compound 403),
2-Chloro-4-(2-methoxy-phenylamino)-2'-methylbenzophenone oxime (Compound 404),
2-Chloro-4-(2-fluoro-phenylamino)-2'-methylbenzophenone oxime (Compound 405),
2-Chloro-4-(2-chloro-phenylamino)-2'-methylbenzophenone oxime (Compound 406),
4-(2-tert-Butoxy-phenylamino)-2-chloro-2'-methylbenzophenone oxime (Compound 407),
2-Chloro-4-(2-hydroxy-phenylamino)-2'-methylbenzophenone oxime (Compound 408),
2-Chloro-4-(3-chloro-phenylamino)-2'-methylbenzophenone oxime (Compound 409),
2-Chloro-4-(2-[1,1,1-trifluoromethyl]-phenylamino)-2'-methylbenzophenone oxime (Compound 410),
4-(4-Bromo-2,5-difluoro-phenylamino)-2-chloro-2'-methylbenzophenone oxime (Compound 411),
2-Chloro-4-(2-ethyl-phenylamino)-2'-methylbenzophenone oxime (Compound 412),
2-Chloro-4-(3-[1,1,1-trifluoromethyl]phenylamino)-2'-methylbenzophenone oxime (Compound 413),
2-Chloro-2'-methyl-4-(2-phenyl-phenylamino)benzophenone oxime (Compound 414),
2-Chloro-2'-methyl-4-(3-phenyl-phenylamino)benzophenone oxime (Compound 415),
2-Chloro-4-(4-fluoro-2-methyl-phenylamino)-2'-methylbenzophenone oxime (Compound 416),
2-Chloro-2'-methyl-4-(3-methyl-phenylamino)benzophenone oxime (Compound 417),
2-Chloro-4-(3-methoxy-phenylamino)-2'-methylbenzophenone oxime (Compound 418),
2-Chloro-4-(4-chloro-phenylamino)-2'-methylbenzophenone oxime (Compound 419),
2-Chloro-2'-methyl-4-(4-phenyl-phenylamino)benzophenone oxime (Compound 420),
4-(4-Bromo-phenylamino)-2-chloro-2'-methylbenzophenone oxime(Compound 421),
4-(4-Bromo-3-fluoro-phenylamino)-2-chloro-2'-methylbenzophenone oxime (Compound 422),
4-(2-Bromo-phenylamino)-2-chloro-2'-methylbenzophenone oxime (Compound 423),
2-Chloro-4-(4-chloro-2-methyl-phenylamino)-2'-methylbenzophenone oxime (Compound 424),
2-Chloro-4-(4-chloro-3-fluoro-phenylamino)-2'-methylbenzophenone oxime (Compound 425),
2-Chloro-4-(3-fluoro-phenylamino)-2'-methylbenzophenone oxime (Compound 426),
2-Chloro-4-(3,5-difluoro-phenylamino)-2'-methylbenzophenone oxime (Compound 427),
4-(3-Bromo-phenylamino)-2-chloro-2'-methylbenzophenone oxime (Compound 428),
2-Chloro-4-(3,4-difluoro-phenylamino)-2'-methylbenzophenone oxime (Compound 429),
2-Chloro-4-(5-fluoro-2-methyl-phenylamino)-2'-methylbenzophenone oxime (Compound 430),
2-Chloro-4-(3-fluoro-2-methyl-phenylamino)-2'-methylbenzophenone oxime (Compound 431),
Ethyl 2-[[3-chloro-4-[(hydroxyimino)(2-methylphenyl)methyl]]phenylamino]benzoate (Compound 432),
2-Chloro-3'-fluoro-4-(4-fluoro-2-methyl-phenylamino)-2'-methylbenzophenone oxime (Compound 433),
2-[[3-Chloro-4-[(hydroxyimino)(2-methylphenyl)methyl]]phenylamino]benzoic acid (Compound 434),
2-Chloro-4-(4-fluoro-2-methyl-N-methyl-phenylamino)-2'-methylbenzophenone oxime (Compound 435),
4-(4-Bromo-2-methyl-phenylamino)-2-chloro-2'-methylbenzophenone oxime (Compound 436),
4-(4-Bromo-2-chloro-phenylamino)-2-chloro-2'-methylbenzophenone oxime (Compound 437),
4-(4-Bromo-2-methyl-phenylamino)-2-chloro-4'-methoxy-2'-methylbenzophenone oxime (Compound 438),
4-(4-Bromo-2-methyl-phenylamino)-2,4'-dichloro-2'-methylbenzophenone oxime (Compound 439),
4-(4-Bromo-2-methyl-phenylamino)-2-chloro-4'-fluoro-2'-methylbenzophenone oxime (Compound 440),
4-(4-Bromo-2-methyl-phenylamino)-2-fluoro-2'-methylbenzophenone oxime (Compound 441),
4-(4-Bromo-2-methyl-phenylamino)-2-chloro-2',5'-dimethyl-benzophenone oxime (Compound 442),
2-Chloro-4-(4-cyano-2-methyl-phenylamino)-2'-methylbenzophenone oxime (Compound 443),
4-(4-Bromo-2-methyl-N-ethyl-phenylamino)-2-chloro-2'-methyl benzophenone oxime (Compound 444),
2-Chloro-4-(4-bromo-2-methyl-phenylamino)-4'-ethoxy-2'-methylbenzophenone oxime (Compound 445),
2,3'-Dichloro-4-(4-bromo-2-methyl-phenylamino)-2'-methylbenzophenone oxime (Compound 446), and salts thereof with pharmaceutically acceptable acids, hydrates and solvates.

The compounds of formulae I, VII, Ia, and Ib can be used in the form of their salts which are formed with pharmaceutically acceptable inorganic or organic acids, such as hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, succinic acid, benzoic acid, maleic acid, these examples being considered as non-limiting for the invention.

As used in the specification, unless specified to the contrary, the following terms have the meaning indicated:

"Alkyl" refers to any univalent group derived from an alkane by removal of a hydrogen atom from any carbon atom, and includes the subclasses of normal alkyl (n-alkyl), and primary, secondary and tertiary alkyl groups respectively, and having the number of carbon atoms specified, including for example $(C_1-C_3)$alkyl, $(C_1-C_5)$alkyl, $(C_5)$alkyl, $(C_6-C_{10})$alkyl, $(C_6-C_{15})$alkyl, methyl, ethyl, n-propy isobutyl, sec-butyl, and t-butyl. Alkane refers to an acyclic branched or unbranched hydrocarbon having the general formula $C_nH_{2n+2}$, and therefore consisting entirely of hydrogen atoms and saturated carbon atoms.

"Olefinic group" refers to a straight or branched acyclic hydrocarbon having one or more carbon-carbon double bonds of either E or Z stereochemistry where applicable, and having the number of carbon atoms specified. The term includes, for example, $(C_2-C_{15})$olefinic group, preferably a $(C_2-C_{15})$alkenyl; $(C_2-C_3)$olefinic group, preferably a $(C_2-C_3)$alkenyl; vinyl; allyl; 1-butenyl; 2-butenyl; and 2-methyl2-propenyl. Olefinic groups having only one carbon-carbon double bond, herein called alkenyl, are preferred.

"Alkoxy" refers broadly to a radical of the formula —OR, where R is alkyl as defined above, for example $(C_1-C_3)$alkoxy, $(C_1-C_2)$alkoxy, methoxy, ethoxy, n-propoxy, and the like.

"$(C_1-C_3)$alkylthio" refers broadly to a radical of the formula —SR, where R is alkyl as defined above and includes methylthio, ethylthio, n-propylthio, and 2-propylthio.

"$(C_1-C_6)$alkylamino" refers broadly to a radical of the formula —NHR or —NR₂, where R is alkyl as defined above having from 1–6 carbon atoms and includes, for example, methylamino, dimethylamino, di-(n-propyl)amino, and n-butyl(ethyl)amino.

"($C_1$–$C_3$)alkoxycarbonyl" refers broadly to a radical of the formula —COOR, where R is alkyl as defined above and includes methoxycarbonyl, ethoxycarbonyl, n-propoxycarbonyl, and i-propoxycarbonyl.

"($C_3$–$C_{10}$)monocyclic hydrocarbon group" includes the saturated cycloalkanes and unsaturated cyclic olefins, such as cycloalkenes having one endocyclic double bond, and having from 3–10 carbon atoms, and includes, for example, ($C_3$–$C_8$)cycloalkyl, cyclopropyl, cyclopentyl, cyclohexyl, and cyclooctyl, ($C_3$–$C_{10}$)cycloalkene group, and ($C_3$–$C_8$) cycloalkene group. Specific examples are cycloprop-2-enyl, cyclobut-2-enyl, cyclopent-2-enyl, cyclohex-3-enyl, and cyclonon-4-enyl.

"Amino" means the group —$NH_2$.

"Carbamoyl" refers to the group —$CONH_2$, —CONHR, and —CONRR' where R and R' represent alkyl as defined above.

"Carboxy" refers broadly to a radical of the formula —COOH.

"Halogen" means the same or different of fluoro, chloro, bromo, and iodo; fluoro, chloro, and bromo being preferred.

Pharmacological Methods

To study the effect of the compound of the present invention in vitro the inhibition of the IL-1β and TNF-α secretion was measured using the following procedure:

Cytokine production was measured in the media from lipopolysaccharide (LPS) stimulated peripheral blood mononuclear cells. The mononuclear cells were isolated from human peripheral blood by Lymphoprep® (Nycomed, Norway) fractionation and suspended in RPMI 1640 (growth medium) with foetal calf serum (FCS, 2%), at a concentration of $5\times10^5$ cells/ml. The cells were incubated in 24-well tissue culture plates in 1 ml aliquots. Test compounds were dissolved in dimethylsulfoxide (DMSO, 10 mM) and were diluted with the medium. Compounds were added to the cells for 30 minutes, then LPS (1 mg/ml final concentration) was added. The plates were incubated for 18 hours, and the concentration of IL-1β and TNF-α in the medium was determined by enzyme-linked immunosorbent assays. The median inhibitory concentrations ($IC_{50}$) of the compounds were calculated. The results are shown in Table 1.

The compounds of the present invention also show similar activities in the ability to inhibit PMN (polymorphonuclear) superoxide secretion which is also indicative of potentially useful anti-inflammatory drugs. The compounds were tested using the following procedure:

Human polymorphonuclear (PMN) granulocytes were isolated from human blood by dextran sedimentation, Lymphoprep® fractionation and hypotonic lysis of contaminating erythrocytes.

Superoxide anion generation was measured as the superoxide dismutase inhibitable reduction of ferricytochrome C (Madhu, S. B. et al, Inflammation, 16, 241, (1992)). The cells were suspended in Hanks' balanced salt solution, and incubated for 10 minutes at 37° C. with test compounds. The cells were primed by the addition of TNF-α (3 ng/ml final concentration) for 10 minutes, and then ferricytochrome C, (final concentration 750 μg/ml), bovine serum albumin (BSA, final concentration 1 mg/ml) and formyl-methionyl-leucyl-phenylalanine (fMLP, final concentration $10^{-7}$ M) were added for 3 minutes. The cells were chilled on ice, and were spun down. The optical densities in the cell-free supernatant was measured in a spectrophotometer. The median inhibitory concentration ($IC_{50}$) of the compounds was calculated. The results are shown in Table 1.

TABLE 1

Inhibition of cytokines and PMN-superoxide production in vitro by compounds of the present invention.

| Comp. No.; | The median inhibition concentration ($IC_{50}$, nM) of | | |
|---|---|---|---|
| | IL-1β | TNF-α | PMN-superoxide |
| 102 | 13 | 4.0 | 6.3 |
| 105 | 25 | 4.0 | 13 |
| 109 | 50 | 7.9 | 20 |
| 116 | 32 | 7.9 | 3.7 |
| 119 | 40 | 16 | 5.0 |
| 130 | 40 | 6.3 | 50 |
| 131 | 13 | 4.0 | 13 |
| 136 | 100 | 8.0 | 100 |
| ref. A) | 13 | 7.1 | 5.0 | ref. A): 4-(2-Aminophenylamino)-2-chloro-2'-methylbenzophenone, compound 106 disclosed in WO 98/32730.

These results show that the compounds of the present invention are able to inhibit the production of IL-1β, TNF-α and PMN-superoxide, and showing a pharmacological activity comparable to a reference compound, thus making them potentially useful in the treatment of inflammatory diseases. It appears from the results shown in Table 1 that some of the compounds of the invention are more selective for one of these inflammatory cytokines than for the other two. This may be an advantage in certain therapeutic situations where a more selective cytokine inhibition is indicated.

To study the compounds of the present invention in vivo the 12-O-tetradecanoylphorbol-13-acetate TPA) induced murine chronic skin inflammation model can be used (De Young, L. M. et al, Agents Actions, 26, 335–341 (1989); Carlson, R. P. et al, Agents Actions, 17, 197–204 (1985); Alford, J. G. et al, Agents Action, 37, (1992); Stanley, P. L. et al, Skin Pharmacol, 4, 262–271 (1991)), cf. description of method in WO 98/32730 hereby incorporated by reference. These results show that the compounds of the present invention are of the same potency compared to known reference compounds, e.g. hydrocortisone with its known side effects, whereas the compounds of the present invention are well tolerated and are non-toxic. Some members of the present class of compounds show a very low systemic absorption, thus making them especially useful in the treatment of various dermatological diseases. In general, they may be administered by e.g. oral, intravenous, intranasal, topically or transdermal routes.

Method of Preparation

The compounds of th e present invention can be prepared in a number of ways well known to those skilled in the art of organic synthesis. The compounds of the present invention can be synthesised using the methods outlined below, together with methods known in the art of synthetic organic chemistry, or variations thereof as appreciated by those skilled in the art. Preferred methods include, but are not limited to, those described below.

The novel compounds of formulae I, VII, Ia, and Ib may be prepared using the reactions and techniques described in this section. The reactions are performed in solvents appropriate to the reagents and materials employed and are suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionality present on various portions of the educt molecule must be compatible with the reagents and reactions proposed. Not all compounds of formula I falling into a given class may be compatible with some of the reaction conditions required in some of the methods described. Such restrictions to the substituents which are compatible with the reaction conditions will be readily apparent to one skilled in the art and alternate methods can be used.

Compounds according to the present invention may be prepared by a process comprising coupling of an amine of the formula III with a bromide, iodide, fluoride, chloride or triflate with the formula II, as shown in scheme 1, where $R_1$, $R_2$, $R_3$, $R_4$, $R_5$, and X are as defined in general formula I, except that an substituents or functional groups which are potentially reactive in the coupling reaction may themselves be protected before the coupling reaction is performed and subsequently removed. The coupling reaction is carried out using any of the methods for the formation of diphenylamines known to one skilled in the art of organic synthesis. The preferred method is the palladium catalysed amination method which comprises coupling of an amine with an arylhalogenide (or aryltriflate) in the presence of a base, a suitable Pd source, and a suitable phosphine ligand in an inert solvent. The palladium compound used in the process is not particularly limited, and as specific examples are palladium(II) acetate, palladium(II) chloride, palladium(II) bromide, dichlorobis(triphenylphosphine)palladium(II), tetrakis(triphenylphosphine)palladium(O), tris(dibenzylideneacetone)dipalladium(O). The preferred ligands include, but are not limited to, racemic or non-racemic 2,2'-bis(diphenylphosphino)-1,1'-binaphthyl (hereinafter refered to as BINAP), tri-o-tolylphosphine, tri-tert-butylphosphine, 1,1'-bis(diphenylphosphino)-ferrocene, bis[(2-diphenylphosphino)phenyl]ether (DPEphos), 2-dicyclohexylphosphanyl-2'-dimethylaminobiphenyl, 2-(di-tert-butylphosphino)biphenyl, and 9,9-dimethyl-4,6-bis(diphenylphosphino)xanthene (Xantphos). The amount of palladium and ligand used in this process is typically in the range 0.1 to 10% by mole relative to the amount of the aromatic halide (or triflate) used. Especially sodium-tert-butoxide (NaOt-Bu) and caesium carbonate ($Cs_2CO_3$) have proven to be the best bases in this process, but other bases may be used as well. The reaction is typically performed at elevated temperature (80–120° C.) in inert solvents like 1,4-dioxane, toluene, benzene and tetrahydrofurane under an inert atmosphere like argon or nitrogen.

Scheme 1

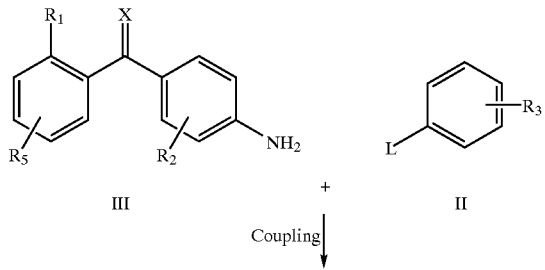

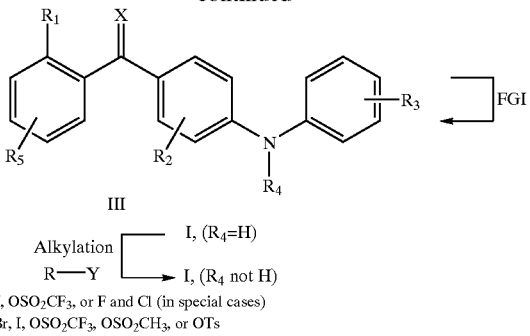

L: Br, I, $OSO_2CF_3$, or F and Cl (in special cases)
Y: Cl, Br, I, $OSO_2CF_3$, $OSO_2CH_3$, or OTs
FGI: Functional group interconversion Compounds according to the present invention in which $R_4$ is not hydrogen may be prepared by a process comprising coupling of an amine of the formula I ($R_4$=H) with an alkylating agent, as shown in scheme 1, where $R_1$, $R_2$, $R_3$, $R_5$, and X are as defined in general formula I, except that any substituents or functional group which are potentially reactive in the coupling reaction may themselves be protected before the coupling reaction is performed and subsequently removed. Typically alkylating agents of the general formula R—Y include, but are not limited to, iodides (Y=I), bromides (Y=Br), chlorides (Y=Cl) and sulfonates (L=$OSO_2R'$, where R' represents methyl, trifluoromethyl or 4-methylphenyl).

Compounds according to the present invention may in special cases be prepared by a simple functional group interconversion (FGI), meaning a standard process, known to those skilled in the art of organic synthesis, where a functional group in compounds with the general formula I is transformed into a different functional group in one or more synthetic steps, leading to a new compound with the general formula I. Examples of such processes are, but are not limited to, hydrolysis of an ester to give an acid under basic conditions; deprotection of a methylether to give a phenol by treatment with e.g. borontribromide ($BBr_3$); and catalytic hydrogenation of an olefin to give a saturated hydrocarbon. Compounds according to the present invention with the general formula I where X=S may be prepared from the ketone (with the general formula I, C=O) by such an FGI process, by using one of the many thiocarbonylating reagent, known to those skilled in the art of organic synthesis. Examples of such thiocarbonylating reagents include, but are not limited to, phosphorous pentasulfide ($P_4S_{10}$), or Lawesson's reagent (2,4-bis(4-methoxyphenyl)-1,3,2,4-dithiaphosphetane-2,4-disulfide) or the like. Compounds according to the present invention with the general formula I where X=N—OH may be prepared from the ketone (with the general formula I, C=O) by treatment with hydroxylamine, or a protected derivative thereof followed by deprotection, in an appropriate solvent like e.g. pyridine or methanol.

Compounds according to the present invention with the general formula III may be prepared by several methods known to those skilled in the art of organic synthesis. One useful sequence is shown in scheme 2. The key step comprising coupling of a bromide (or iodide) with the general formula VI with an acid chloride with the general formula V to afford the benzophenone with the general formula IV. This compound IV may then be reduced to the corresponding amine with the general formula III by treatment with standard reducing agents. Examples of such reducing agents include, but are not limited to, stannous chloride dihydrate; hydrogen, ammonium formiate, or hydrazine hydrate and a catalytic amount of palladium on carbon. The coupling reaction is done by transforming the bromide (VI) into a reactive organometallic intermediate, e.g. by treatment with butyllithium to afford the lithium derivative or by treatment with magnesium to afford the magnesium derivative.

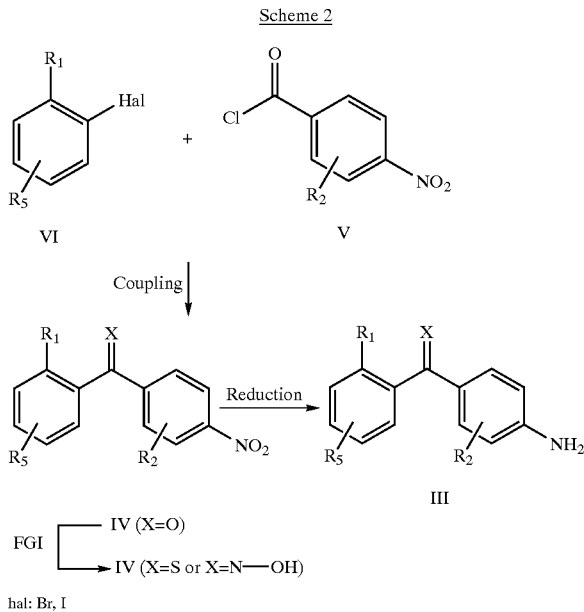

Scheme 2 hal: Br, I

The reactivity of this intermediate is then modulated by transmetalation to e.g. zinc, by treatment with $ZnCl_2$, $ZnBr_2$, or $ZnI_2$. This organozinc compund is then coupled with the acid chloride, with the general formula V, under the influence of a palladium(O) complex in catalytic amount. Examples of such catalyst include but are not particularly limited to tetrakis(triphenylphosphine)palladium(O), tetrakis(triphenylarsine)palladium(O), dichlorobis(triphenylphosphine)palladium(II), or benzylchlorobis(triphenylphosphine)palladium(II).

As shown on scheme 2 compounds with the general formula IV (X=O) may be transformed by an FGI process to give compounds with the general formula IV (X=S or X=N—OH) as described above. This is only to illustrate the flexibility in the synthesis and in general the described sequence of processes is only one of many possible strategies for the synthesis of compound of the present invention. That is, it may be more advantageous in some cases to alter the sequence of the processes described above. The described sequence of processes is not considered as being limited for the preparation of the compounds of the present invention with the general formula I and alteration of the reaction sequence is an obvious alternative for those skilled in the art of organic synthesis.

The present compounds are intended for use in pharmaceutical compositions which are useful in the treatment of the above mentioned diseases.

The amount required of a compound of formula I, VII, Ib and Ia (hereinafter referred to as the active compound or active ingredient) for therapeutic effect will, of course, vary both with the particular compound, the route of administration and the mammal under treatment. A suitable dose of an active compound for systemic treatment is 0.1 to 200 mg/kg bodyweight, the most preferred dosage being 0.2 to 50 mg/kg of mammal bodyweight, administered one or more times daily.

While it is possible for an active ingredient to be administered alone as the raw chemical, it is preferable to present it as a pharmaceutical formulation. Conveniently, the active ingredient comprises from 0.1% to 100% by weight of the formulation. Conveniently, dosage units of a formulation contain between 0.07 mg and 1 g of the active ingredient. For topical administration, the active ingredient preferably comprises from 1% to 20% by weight of the formulation but the active ingredient may comprise as much as 50% w/w. Formulations suitable for nasal or buccal administration may comprise 0.1% to 20% w/w. for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include those in a form suitable for oral, ophthalmic, rectal, parenteral (including subcutaneous, intramuscular and intravenous), transdermal, intra-articular, topical, nasal, or buccal administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

Formulations suitable for administration to the nose or buccal cavity include powder, self-propelling and spray formulations, such as aerosols and atomizers.

In addition to the aforementioned ingredients, the formulations of this invention may include one or more additional ingredients.

The compositions may further contain other therapeutically active compounds usually applied in the treatment of the above mentioned pathological conditions, for instance glucocorticoids, vitamin D analogues, anti-histamines, platelet activating factor (PAF) antagonists, anticolinergic agents, methyl xanthines, β-adrenergic agents, COX-2 inhibitors, salicylates, indomethacin, flufenamate, naproxen, timegadine, gold salts, penicillamine, serum cholesterol-reducing agents, retinoids, zinc salts, and salicylazosulfapyridin (Salazopyrin).

The novel compounds of the invention are of value in the human and veterinary practice as systemic and topical therapeutic agents for the treatment and prevention of diseases. The novel compounds show anti-acne properties and, i.a., anti-inflammatory and cytokine regulating effects possibly due to MAP kinase inhibition, and are useful in the treatment and prophylaxis of asthma, allergy, arthritis, including rheumatoid arthritis and spondyloarthritis, gout, atherosclerosis, chronic inflammatory bowel disease (Crohn's disease), proliferative and inflammatory skin disorders, such as psoriasis, atopic dermatitis or acne; uveitis, septic shock, AIDS, and osteoporosis.

The invention will now be further described in the following non-limiting general procedures, preparations and examples.

EXAMPLES

General procedures, preparations and Examples

Specific examples of compounds of formula I are listed in Table 2.

All melting points are uncorrected. For $^1$H and $^{13}$C nuclear magnetic resonance (NMR) spectra (300 MHz for $^1$H) chemical shift values (δ) (in ppm) are quoted, unless otherwise specified, for deuteriochloroform and hexadeuterodimethylsulfoxide solutions relative to internal tetramethylsilane (δ0.00) or chloroform ($^1$H NMR δ7.25, $^{13}$C NMR δ76.81). The value for a multiplet (m), either defined (doublet (d), triplet (t), quartet (q)) or not at the approximate mid point is given unless a range is quoted (s singlet, b broad). The organic solvents used were anhydrous. The term "chromatography" refers to column chromatography using the flash technique and was performed on silica gel.

The following abbreviations have been used throughout this specification: BINAP=racemic or non-racemic 2,2'-bis(diphenylphosphino)-1,1'-binaphthyl, CDCl$_3$= deuteriochloroform, DMSO-d$_6$=hexadeuterodimethylsulfoxide, DMSO=dimethylsulfoxide, EtOAc=ethyl acetate, Et$_2$O=diethylether, Pd$_2$(dba)$_3$=tris(dibenzylideneacetone)dipalladium(O), THF=tetrahydrofurane, TLC=thin layer chromatography.

TABLE 2

Compounds of General formula I

| Comp. No. Example No. | X | R$_1$ | R$_2$ | R$_3$ | R$_4$ | R$_5$ |
|---|---|---|---|---|---|---|
| 101, Ex. 1 | O | Me | 2-Cl | 2-CN | H | H |
| 102, Ex. 2 | O | Me | 2-Cl | 2-Me | H | H |
| 103, Ex. 3 | O | Me | 2-Cl | H | H | H |
| 104, Ex. 4 | O | Me | 2-Cl | 2-OMe | H | H |

TABLE 2-continued

Compounds of General formula I

| Comp. No. Example No. | X | R$_1$ | R$_2$ | R$_3$ | R$_4$ | R$_5$ |
|---|---|---|---|---|---|---|
| 105, Ex. 5 | O | Me | 2-Cl | 2-F | H | H |
| 106, Ex. 6 | O | Me | 2-Cl | 2-Cl | H | H |
| 107, Ex. 7 | O | Me | 2-Cl | 2-Ot-Bu | H | H |
| 108, Ex. 8 | O | Me | 2-Cl | 2-OH | H | H |
| 109, Ex. 9 | O | Me | 2-Cl | 3-Cl | H | H |
| 110, Ex. 10 | O | Me | 2-Cl | 2-CF$_3$ | H | H |
| 111, Ex. 11 | O | Me | 2-Cl | 2,5-di-F, 4-Br | H | H |
| 112, Ex. 12 | O | Me | 2-Cl | 2-Et | H | H |
| 113, Ex. 13 | O | Me | 2-Cl | 3-CF$_3$ | H | H |
| 114, Ex. 14 | O | Me | 2-Cl | 2-phenyl | H | H |
| 115, Ex. 15 | O | Me | 2-Cl | 3-phenyl | H | H |
| 116, Ex. 16 | O | Me | 2-Cl | 2-Me, 4-F | H | H |
| 117, Ex. 17 | O | Me | 2-Cl | 3-Me | H | H |
| 118, Ex. 18 | O | Me | 2-Cl | 3-OMe | H | H |
| 119, Ex. 19 | O | Me | 2-Cl | 4-Cl | H | H |
| 120, Ex. 20 | O | Me | 2-Cl | 4-phenyl | H | H |
| 121, Ex. 21 | O | Me | 2-Cl | 4-Br | H | H |
| 122, Ex. 22 | O | Me | 2-Cl | 3-F, 4-Br | H | H |
| 123, Ex. 23 | O | Me | 2-Cl | 2-Br | H | H |
| 124, Ex. 24 | O | Me | 2-Cl | 2-Me, 4-Cl | H | H |
| 125, Ex. 25 | O | Me | 2-Cl | 3-F, 4-Cl | H | H |
| 126, Ex. 26 | O | Me | 2-Cl | 3-F | H | H |
| 127, Ex. 27 | O | Me | 2-Cl | 3,5-di-F | H | H |
| 128, Ex. 28 | O | Me | 2-Cl | 3-Br | H | H |
| 129, Ex. 29 | O | Me | 2-Cl | 3,4-di-F | H | H |
| 130, Ex. 30 | O | Me | 2-Cl | 2-Me, 5-F | H | H |
| 131, Ex. 31 | O | Me | 2-Cl | 2-Me, 3-F | H | H |
| 132, Ex. 32 | O | Me | 2-Cl | 2-COOEt | H | H |
| 133, Ex. 33 | O | Me | 2-Cl | 2-Me, 4-F | H | 3-F |
| 134, Ex. 34 | O | Me | 2-Cl | 2-COOH | H | H |
| 135, Ex. 35 | O | Me | 2-Cl | 2-Me, 4-F | Me | H |
| 136, Ex. 36 | O | Me | 2-Cl | 2-Me, 4-Br | H | H |
| 137, Ex. 37 | O | Me | 2-Cl | 2-Cl, 4-Br | H | H |
| 138, Ex. 38 | O | Me | 2-Cl | 2-Me, 4-Br | H | 4-OMe |
| 139, Ex. 39 | O | Me | 2-Cl | 2-Me, 4-Br | H | 4-Cl |
| 140, Ex. 40 | O | Me | 2-Cl | 2-Me, 4-Br | H | 4-F |
| 141, Ex. 41 | O | Me | 2-F | 2-Me, 4-Br | H | H |
| 142, Ex. 42 | O | Me | 2-Cl | 2-Me, 4-Br | H | 5-Me |
| 143, Ex. 43 | O | Me | 2-Cl | 2-Me, 4-CN | H | H |
| 144, Ex. 44 | O | Me | 2-Cl | 2-Me, 4-Br | Et | H |
| 145, Ex. 45 | O | Me | 2-Cl | 2-Me, 4-Br | H | 4-OEt |
| 146, Ex. 46 | O | Me | 2-Cl | 2-Me, 4-Br | H | 3-Cl |

The numbering in Table 2 refers to the numbering in the formula below

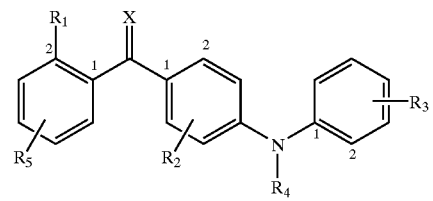

General Procedure 1

Coupling of compounds of the general formula II with compounds of the general formula III to give compounds of the general formula I, or a protected derivative thereof.

A Schlenk tube was charged with the base (Cs$_2$CO$_3$ or NaOt-Bu, 1.4 mmol), Pd$_2$(dba)$_3$ (0.05 mmol), and BINAP (0.075 mmol). The tube was capped with a rubber septum and flushed with argon for 5 min, then a solution of a halogenide (1.1 mmol), with the general formula II, and an amine (1.0 mmol), with the general formula III, in 1,4-dioxane or toluene (5.0 ml) was added via cannula. The resulting solution was first stirred under argon at room temperature for 15 min and then at 100° C. for 4–20 h or until the starting materials had disappeared as seen on TLC. The reaction mixture was allowed to cool to room temperature. The reaction mixture was poured into a mixture of EtOAc and water. The organic phase was separated, dried (MgSO$_4$), filtered and concentrated in vacuo. The residue was purified either by chromatography and/or crystallization to afford the coupled product with the general formula I, or a protected derivative thereof.

General Procedure 2

Coupling of compounds of the general formula VI with compounds of the general formula V to give compounds of the general formula IV, or a protected derivative thereof.

The bromide (80 mmol) with the general formula VI was disssolved in dry THF (65 ml) and cooled with stirring to −78° C. under an atmosphere of argon. n-Butyllithium (80 mmol, 1.6 M solution in hexane) was then added dropwise, keeping the internal temperature below −65° C. and stirring the resulting mixture for further 15 min. A THF solution of ZnCl$_2$ (100 mmol, 1.0 M) was added dropwise and the reaction mixture was allowed to warm to room temperature. After 2 h the reaction mixture was cooled to 0° C., and tetrakis(triphenylphosphine)palladium(O) (4.0 mmol) was added followed by the dropwise addition of the acid chloride (84 mmol), with the general formula V, in THF. The reaction mixture was allowed to warm to 20° C. and stirred for ca 16 h. The resulting yellow solution, was filtered and the filtrate poured into a mixture of EtOAc/water 1:1, shaken and separated. The aqueous phase was extracted with two more portions of EtOAc. The organic phases were combined, dried (MgSO$_4$), filtered, and concentrated in vacuo to afford the crude product. Further purification was done by flash chromatography and/or crystallization to give the title compound IV, or a protected derivative thereof.

General Procedure 3

Reduction of compounds of the general formula IV with stannous chloride dihydrate to give compounds of the general formula III, or a protected derivative thereof.

A mixture of a compound with the general formula IV (5 mmol) and stannous chloride dihydrate (5.64 g, 25 mmol) in absolute ethanol (50 ml) was heated to 70° C. under argon. After 1 hour, or until the starting material had disappeared as seen on TLC, the solution was allowed to cool to room temperature and then poured into ice/water. The pH was made alkaline by the addition of saturated sodium hydroxide (50 ml) before being extracted with ethyl acetate (3×100 ml). The organic phase was dried (MgSO$_4$), filtered and evaporated to afford the crude product. The crude product was further purified either by crystallization or flash chromatography to yield the title compound or a protected derivative thereof.

Preparation 1

2-Chloro-2'-methyl-4-nitrobenzophenone (Compound 201)

General Procedure: 2
  Starting compound VI: 2-Bromotoluene
  Starting compound V: 2-Chloro-4-nitro-benzoyl chloride
  Purification: Chromatography using EtOAc/pentane 1:9 as eluant
  $^{13}$C NMR (CDCl$_3$): δ195.1, 148.9, 145.5, 140.6, 135.0, 133.1, 132.7, 132.4, 131.9, 130.0, 125.9, 125.4, 121.9, 21.5

Preparation 2

4-Amino-2-chloro-2'-methylbenzophenone (Compound 202)

General Procedure: 3
  Starting compound IV: 2-Chloro-2'-methyl-4-nitrobenzophenone (Compound 201)
  Purification: Chromatography using EtOAc/pentane 1:9 followed by 1:4 as eluant
  $^{13}$C NMR (CDCl$_3$): δ196.7, 150.5, 139.5, 137.6, 135.1, 133.9, 131.2, 130.7, 129.5, 127.5, 125.3, 116.0, 112.2, 20.3

Preparation 3

2-Chloro-3'-fluoro-2'-methyl-4-nitrobenzophenone (Compound 203)

General Procedure: 2
  Starting compound VI: 2-Bromo-3-fluorotoluene
  Starting compound V: 2-Chloro-4-nitro-benzoyl chloride
  Purification: Chromatography using EtOAc/pentane 1:20 as eluant
  $^{13}$C NMR (CDCl$_3$): δ194.3, 161.8, 149.1, 144.8, 137.6, 133.0, 130.3, 127.2, 126.9, 126.8, 125.5, 122.0, 119.8, 11.7

Preparation 4

4-Amino-2-chloro-3'-fluoro-2'-methylbenzophenone (Compound 204)

General Procedure: 3
  Starting compound IV: 2-Chloro-3'-fluoro-2'-methyl-4-nitrobenzophenone (Compound 203)
  Purification: Chromatography using EtOAc/pentane 1:9 followed by CH$_2$Cl$_2$ as eluant
  $^{13}$C NMR (CDCl$_3$): δ195.2, 161.5, 150.7, 142.1, 135.5, 134.2, 127.1, 126.5, 124.5, 117.2, 116.0, 112.2, 11.5

Preparation 5

2-Chloro-4'-methoxy-2'-methyl-4-nitrobenzophenone (Compound 205)

General Procedure: 2
  Starting compound VI: 2-Bromo-5-methoxytoluene
  Starting compound V: 2-Chloro-4-nitro-benzoyl chloride
  Purification: Crystallization from a MeOH/cyclohexane 10:1
  $^{13}$C NMR (CDCl$_3$): δ193.3, 163.3, 148.6, 146.3, 144.3, 135.5, 132.4, 129.6, 127.5, 125.3, 121.9, 118.1, 110.9, 55.5, 22.4

Preparation 6

4-Amino-2-chloro-4'-methoxy-2'-methylbenzophenone (Compound 206)

General Procedure: 3
  Starting compound IV: 2-Chloro-4'-methoxy-2'-methyl-4-nitrobenzophenone (Compound 205)
  Purification: Filtered through a short column of silica gel
  $^{13}$C NMR (CDCl$_3$): δ195.7, 161.7, 149.6, 141.6, 134.2, 133.3, 132.8, 131.4, 129.1, 117.0, 115.8, 112.4, 110.3, 55.3, 21.3

Preparation 7

2,4'-Dichloro-2'-methyl-4-nitrobenzophenone (Compound 207)

General Procedure: 2
  Starting compound VI: 2-Bromo-5-chlorotoluene
  Starting compound V: 2-Chloro-4-nitro-benzoyl chloride
  Purification: Chromatography using EtOAc/pentane 1:15 followed by 1:10 as eluant
  $^{13}$C NMR (CDCl$_3$): δ194.1, 149.0, 145.0, 142.6, 139.4, 133.5, 133.1, 132.7, 132.5, 130.1, 126.1, 125.5, 122.0, 21.4

Preparation 8

4-Amino-2,4'-dichloro-2'-methylbenzophenone (Compound 208)

General Procedure: 3
  Starting compound IV: 2,4'-Dichloro-2'-methyl-4-nitrobenzophenone (Compound 207)
  $^{13}$C NMR (CDCl$_3$): δ195.4, 150.5, 139.8, 137.9, 136.5, 135.1, 133.7, 131.2, 130.9, 127.5, 125.6, 115.9, 112.3, 20.2

Preparation 9

2-Chloro-4'-fluoro-2'-methyl-4-nitrobenzophenone
(Compound 209)

General Procedure: 2
  Starting compound VI: 2-Bromo-5-fluorotoluene
  Starting compound V: 2-Chloro-4-nitro-benzoyl chloride
  Purification: Chromatography using EtOAc/pentane 1:20 as eluant
  $^{13}$C NMR (CDCl$_3$): δ193.7, 165.1, 148.9, 145.3, 144.6, 134.7, 132.6, 131.4, 129.9, 125.5, 122.0, 119.5, 113.0, 21.8

Preparation 10

4-Amino-2-chloro-4'-fluoro-2'-methylbenzophenone
(Compound 210)

General Procedure: 3
  Starting compound IV: 2-Chloro-4'-fluoro-2'-methyl-4-nitrobenzophenone (Compound 209)
  Purification: Filtered through a short column of silica gel
  $^{13}$C NMR (CDCl$_3$): δ195.4, 163.9, 150.3, 141.5, 135.5, 134.9, 133.5, 132.2, 128.0, 118.1, 115.9, 112.4, 112.3, 20.6

Preparation 11

2-Fluoro-4-nitro-2'-methylbenzophenone
(Compound 211)

General Procedure: 2
  Starting compound VI: 2-Bromotoluene
  Starting compound V: 2-Fluoro-4-nitro-benzoyl chloride
  Purification: Crystallization from a mixture of MeOH/cyclohexane 6:1
  $^{13}$C NMR (CDCl$_3$): δ193.1, 159.9, 150.3, 139.3, 136.4, 133.8, 132.6, 132.1, 131.7, 130.8, 125.8, 119.4, 112.4, 21.0

Preparation 12

4-Amino-2-fluoro-2'-methylbenzophenone
(Compound 212)

General Procedure: 3
  Starting compound IV: 2-Fluoro-4-nitro-2'-methylbenzophenone (Compound 211)
  Purification: Filtered through a short column of silica gel
  $^{13}$C NMR (CDCl$_3$): δ194.3, 163.8, 153.0, 140.7, 136.1, 134.0, 130.8, 129.9, 127.9, 125.3, 116.8, 110.1, 101.3, 19.8

Preparation 13

2-Chloro-2',5'-dimethyl-4-nitrobenzophenone
(Compound 213)

General Procedure: 2
  Starting compound VI: 2-Bromo-1,4-dimethylbenzene
  Starting compound V: 2-Chloro-4-nitro-benzoyl chloride
  Purification: Filtered through a short column of silica gel
  $^{13}$C NMR (CDCl$_3$): δ195.3, 148.9, 145.6, 137.4, 135.5, 135.0, 133.9, 132.8, 132.3, 132.2, 130.0, 125.5, 121.9, 21.1, 20.8

Preparation 14

4-Amino-2-chloro-2',5'-dimethylbenzophenone
(Compound 214)

General Procedure: 3
  Starting compound IV: 2-Chloro-2',5'-dimethyl-4-nitrobenzophenone (Compound 213)
  Purification: Filtered through a short column of silica gel
  $^{13}$C NMR (CDCl$_3$): δ196.8, 150.2, 139.3, 135.1, 134.9, 134.5, 133.8, 131.4, 131.1, 130.0, 128.0, 116.0, 112.2, 20.8, 19.9

Preparation 15

2-Chloro-4'-ethoxy-2'-methyl-4-nitrobenzophenone
(Compound 215)

General Procedure: 2
  Starting compound VI: 2-Bromo-5-ethoxytoluene
  Starting compound V: 2-Chloro-4-nitro-benzoyl chloride
  Purification: Crystallization from a mixture of MeOH/cyclohexane 10:1
  $^{13}$C NMR (CDCl$_3$): δ193.3, 162.8, 148.5, 146.4, 144.3, 135.5, 132.4, 129.5, 127.3, 125.3, 121.9, 118.5, 111.2, 63.8, 22.5, 14.6

Preparation 16

4-Amino-2-chloro-4'-ethoxy-2'-methylbenzophenone
(Compound 216)

General Procedure: 3
  Starting compound IV: 2-Chloro-4'-ethoxy-2'-methyl-4-nitrobenzophenone
  Purification: Filtered through a short column of silica gel
  $^{13}$C NMR (CDCl$_3$): δ195.7, 161.2, 149.6, 141.7, 134.2, 133.4, 132.7, 131.1, 129.2, 117.5, 115.7, 112.4, 110.8, 63.5, 21.4, 14.7

Preparation 17

2,3'-Dichloro-2'-methyl-4-nitrobenzophenone
(Compound 217)

General Procedure: 2
  Starting compound VI: 2-Bromo-3-chlorotoluene
  Starting compound V: 2-Chloro-4-nitro-benzoyl chloride
  Purification: Crystallization from a mixture of MeOH/cyclohexane 9:1
  $^{13}$C NMR (CDCl$_3$): δ194.6, 149.2, 144.5, 138.2, 137.3, 137.0, 133.5, 133.2, 130.7, 129.0, 126.5, 125.7, 122.0, 17.3

Preparation 18

4-Amino-2,3'-dichloro-2'-methylbenzophenone
(Compound 218)

General Procedure: 3
  Starting compound IV: 2,3'-Dichloro-2'-methyl-4-nitrobenzophenone
  Purification: Filtered through a short column of silica gel
  $^{13}$C NMR (CDCl$_3$): δ195.3, 150.9, 142.4, 135.8, 135.8, 134.8, 134.6, 131.0, 126.8, 126.7, 126.4, 116.2, 112.2, 17.1

Example 1

2-[[3-Chloro-4-(2-methylbenzoyl)]phenylamino]benzonitrile (Compound 101)

To a solution of 4-amino-2-chloro-2'-methylbenzophenone (10 mmol) and 2-fluorobenzonitrile (10 mmol) in DMSO (25 ml) was added potassium tert-butoxide (2.36 g, 21 mmol). The reaction mixture was stirred at room temperature for 40 hours, diluted with water (300 ml) and extracted with ethyl acetate (3×100 ml). The organic phase was dried (MgSO$_4$), filtered and concentrated in vacuo to afford the crude product. The crude product was further purified by flash chromatography using EtOAc/pentane 1:9 as eluent to yield the title compound, which crystallized after trituration in pentane.
  $^{13}$C NMR (CDCl$_3$): δ196.4, 144.4, 144.3, 138.6, 134.1, 133.6, 133.5, 132.7, 131.6, 131.5, 130.3, 125.5, 122.0, 119.7, 117.4, 116.9, 116.4, 101.9, 20.7

Example 2

2-Chloro-2'-methyl-4-(2-methyl-phenylamino)benzophenone (Compound 102)

General Procedure: 1
  Starting compound II: 2-Bromotoluene
  Starting compound III: 4-Amino-2-chloro-2'-methylbenzophenone
  Solvent: 1,4-Dioxane Base: NaOt-Bu
Purification: Chromatography using EtOAc/pentane 1:9 as eluant
$^{13}$C NMR (CDCl$_3$): δ196.5, 149.0, 139.4, 138.1, 137.8, 135.2, 133.7, 132.3, 131.4, 131.2, 130.7, 129.6, 128.4, 127.1, 125.4, 125.3, 123.8, 115.8, 112.2, 20.4, 17.9

Example 3

2-Chloro-2'-methyl-4-(phenylamino)benzophenone (Compound 103)

General Procedure: 1
Starting compound II: bromobenzene
Starting compound III: 4-Amino-2-chloro-2'-methylbenzophenone
Solvent: 1,4-Dioxane
Base: NaOt-Bu
Purification: Chromatography using EtOAc/pentane 1:9 as eluant
$^{13}$C NMR (CDCl$_3$): δ196.5, 147.8, 140.2, 139.2, 137.9, 135.0, 133.5, 131.3, 130.8, 129.7, 129.6, 129.2, 125.4, 123.8, 121.0, 116.4, 112.9, 20.4

Example 4

2-Chloro-4-(2-methoxy-phenylamino)-2'-methylbenzophenone (Compound 104)

General Procedure: 1
Starting compound II: 2-Bromoanisole
Starting compound III: 4-Amino-2-chloro-2'-methylbenzophenone
Solvent: 1,4-Dioxane
Base: NaOt-Bu
Purification: Chromatography using EtOAc/pentane 1:9 as eluant
$^{13}$C NMR (CDCl$_3$): δ196.4, 149.9, 147.3, 139.2 137.9, 134.9, 133.4, 131.2, 130.8, 129.7, 129.7, 129.2, 125.4, 123.1, 120.8, 118.6, 117.0, 113.4, 111.1, 55.6, 20.4

Example 5

2-Chloro-4-(2-fluoro-phenylamino)-2'-methylbenzophenone (Compound 105)

General Procedure: 1
Starting compound II: 1-Bromo-2-fluorobenzene
Starting compound III: 4-Amino-2-chloro-2'-methylbenzophenone
Solvent: Toluene
Base: Cs$_2$CO$_3$
Purification: Chromatography using EtOAc/pentane 1:9 as eluant
$^{13}$C NMR (CDCl$_3$): δ196.5, 154.5, 146.7, 138.9, 138.1, 134.8, 133.2, 131.4, 131.0, 130.2, 129.9, 128.6, 125.4, 124.6, 124.0, 121.2, 117.0, 116.2, 113.6, 20.5

Example 6

2-Chloro-4-(2-chloro-phenylamino)-2'-methylbenzophenone (Compound 106)

General Procedure: 1
Starting compound II: 1-Bromo-2-chlorobenzene
Starting compound III: 4-Amino-2-chloro-2'-methylbenzophenone
Solvent: 1,4-Dioxane
Base: NaOt-Bu
Purification: Chromatography using EtOAc/pentane 1:9 as eluant
$^{13}$C NMR (CDCl$_3$): δ196.4, 146.1, 138.7, 138.3, 137.5, 134.7, 133.1, 131.4, 131.1, 130.9, 130.2, 130.0, 127.7, 125.4, 124.6, 123.5, 119.5, 118.0, 114.6, 20.6

Example 7

4-(2-tert-Butoxy-phenylamino)-2-chloro-2'-methylbenzophenone (Compound 107)

General Procedure: 1
Starting compound II: 2-Bromo-1-tert-butoxybenzene
Starting compound III: 4-Amino-2-chloro-2'-methylbenzophenone
Solvent: 1,4-Dioxane
Base: NaOt-Bu
Purification: Chromatography using Et$_2$O/pentane 1:4 as eluant
$^{13}$C NMR (CDCl$_3$): δ196.4, 147.1, 145.9, 139.1, 138.0, 135.0, 134.9, 133.5, 131.3, 130.8, 129.7, 129.4, 125.4, 123.5, 123.4, 122.5, 118.8, 116.7, 113.3, 80.3, 29.0, 20.5

Example 8

2-Chloro-4-(2-hydroxy-phenylamino)-2'-methylbenzophenone (Compound 108)

A solution of 4-(2-tert-butoxy-phenylamino)-2-chloro-2'-methylbenzophenone (Compound 107) (1.33 g, 3.4 mmol) in a mixture of CH$_2$Cl$_2$ (5 ml) and trifluoroethanol (20 ml) was cooled to −5° C. under argron. Trifluoroacetic acid (423 mg, 3.7 mmol) was added dropwise and the reaction mixture was allowed to come to room temperature over 1 h. After 23 h at room temperature the reaction mixture was poured into saturated NaHCO$_3$ and then extracted with EtOAc and CH$_2$Cl$_2$. The organic phases was collected, dried (MgSO$_4$), filtered, and concentrated in vacuo to give the crude product. This was further purified by flash chromatography using EtOAc/pentane 1:4 as eluant.
$^{13}$C NMR (CDCl$_3$): δ197.3, 150.2, 149.2, 139.1, 137.8, 135.1, 133.6, 131.3, 131.0, 129.7, 128.7, 127.0, 126.5, 125.4, 124.2, 121.0, 116.2, 116.1, 112.6, 20.4

Example 9

2-Chloro-4-(3-chloro-phenylamino)-2'-methylbenzophenone (Compound 109)

General Procedure: 1
Starting compound II: 1-Bromo-3-chlorobenzene
Starting compound III: 4-Amino-2-chloro-2'-methylbenzophenone
Solvent: 1,4-Dioxane
Base: NaOt-Bu
Purification: Chromatography using EtOAc/pentane 1:9 as eluant
$^{13}$C NMR (CDCl$_3$): δ196.5, 146.6, 141.8, 138.8, 138.1, 135.3, 134.9, 133.2, 131.4, 131.1, 130.6, 130.3, 129.9, 125.4, 123.4, 120.1, 118.2, 117.3, 113.7, 20.5

Example 10

2-Chloro-4-(2-[1,1,1-trifluoromethyl]-phenylamino)-2'-methylbenzophenone (Compound 110)

General Procedure: 1
Starting compound II: 1-Bromo-2-(1,1,1-trifluoromethyl)benzene
Starting compound III: 4-Amino-2-chloro-2'-methylbenzophenone
Solvent: 1,4-Dioxane
Base: NaOt-Bu
Purification: Chromatography using EtOAc/pentane 1:9 as eluant
$^{13}$C NMR (CDCl$_3$): δ196.4, 146.6, 139.0, 138.6, 138.3, 134.7, 133.1, 133.0, 131.4, 131.2, 131.0, 130.0, 127.2, 125.4, 123.8, 123.3, 122.3, 117.9, 114.5, 20.6

Example 11

4-(4-Bromo-2,5-difluoro-phenylamino)-2-chloro-2'-methylbenzophenone (Compound 111)

General Procedure: 1
Starting compound II: 1-iodo-4-bromo-2,5-difluorobenzene
Starting compound III: 4-Amino-2-chloro-2'-methylbenzophenone
Solvent: 1,4-Dioxane
Base: NaOt-Bu
Purification: Chromatography using EtOAc/pentane 1:9 as eluant $^{13}$C NMR (CDCl$_3$): δ196.4, 155.6, 149.3, 144.5, 138.5, 138.2, 134.6, 132.8, 132.2, 131.6, 131.4, 130.2, 125.5, 120.1, 118.7, 115.1, 106.3, 20.7

Example 12

2-Chloro-4-(2-ethyl-phenylamino)-2'-methylbenzophenone (Compound 112)

General Procedure: 1
Starting compound II: 2-Bromo-ethylbenzene
Starting compound III: 4-Amino-2-chloro-2'-methylbenzophenone
Solvent: 1,4-Dioxane
Base: NaOt-Bu
Purification: Chromatography using EtOAc/pentane 1:9 as eluant $^{13}$C NMR (CDCl$_3$): δ196.4, 149.5, 139.4, 138.6, 137.8, 137.5, 135.2, 133.7, 131.2, 130.7, 129.5, 128.2, 127.0, 125.9, 125.3, 124.7, 115.6, 112.0, 24.4, 20.4, 14.3

Example 13

2-Chloro-4-(3-[1,1,1-trifluoromethyl]phenylamino)-2'-methylbenzophenone (Compound 113)

General Procedure: 1
Starting compound II: 1-Bromo-3-(1,1,1-trifluoromethyl)benzene
Starting compound III: 4-Amino-2-chloro-2'-methylbenzophenone
Solvent: 1,4-Dioxane
Base: NaOt-Bu
Purification: Chromatography using EtOAc/pentane 1:9 as eluant $^{13}$C NMR (CDCl$_3$): δ196.5, 146.4, 141.2, 138.7, 138.2, 134.9, 133.2, 132.2, 131.2, 131.2, 130.7, 130.2, 130.0, 125.5, 122.9, 123.8, 119.8, 117.5, 116.7, 113.7, 20.6

Example 14

2-Chloro-2'-methyl-4-(2-phenyl-phenylamino)benzophenone (Compound 114)

General Procedure: 1
Starting compound II: 2-Bromobiphenyl
Starting compound III: 4-Amino-2-chloro-2'-methylbenzophenone
Solvent: 1,4-Dioxane
Base: NaOt-Bu
Purification: Chromatography using EtOAc/pentane 1:9 repeated by chromatography using CH$_2$Cl$_2$/pentane 1:1 as eluant $^{13}$C NMR (CDCl$_3$): δ196.4, 148.1, 139.1, 138.4, 138.0, 137.2, 135.0, 134.6, 133.5, 131.3, 131.2, 130.8, 129.7, 129.3, 129.2, 128.9, 128.4, 127.8, 125.3, 124.2, 121.6, 116.5, 113.0, 20.5

Example 15

2-Chloro-2'-methyl-4-(3-phenyl-phenylamino)benzophenone (Compound 115)

General Procedure: 1
Starting compound II: 3-Bromobiphenyl
Starting compound III: 4-Amino-2-chloro-2'-methylbenzophenone
Solvent: 1,4-Dioxane
Base: NaOt-Bu
Purification: Chromatography using EtOAc/pentane 1:9 as eluant $^{13}$C NMR (CDCl$_3$): δ196.5, 147.7, 143.0, 140.7, 140.5, 139.1, 138.0, 135.1, 133.5, 131.3, 130.9, 130.0, 129.7, 129.4, 128.9, 127.7, 127.1, 125.4, 122.7, 119.7, 116.7, 113.0, 20.5

Example 16

2-Chloro-4-(4-fluoro-2-methyl-phenylamino)-2'-methylbenzophenone (Compound 116)

General Procedure: 1
Starting compound II: 2-Bromo-5-fluorotoluene
Starting compound III: 4-Amino-2-chloro-2'-methylbenzophenone
Solvent: 1,4-Dioxane
Base: Cs$_2$CO$_3$
Purification: Chromatography using EtOAc/pentane 1:4 as eluant $^{13}$C NMR (CDCl$_3$): δ196.5, 160.5, 149.6, 139.3, 137.8, 136.3, 135.3, 133.7, 131.2, 130.7, 129.5, 128.2, 127.1, 125.3, 117.8, 115.2, 113.8, 111.6, 20.4, 18.1

Example 17

2-Chloro-2'-methyl-4-(3-methyl-phenylamino)benzophenone (Compound 117)

General Procedure: 1
Starting compound II: 3-Bromotoluene
Starting compound III: 4-Amino-2-chloro-2'-methylbenzophenone
Solvent: 1,4-Dioxane
Base: NaO-t-Bu
Purification: Chromatography using CH$_2$Cl$_2$/pentane 2:1 as eluant $^{13}$C NMR (CDCl$_3$): δ196.5, 148.0, 140.1, 139.6, 139.2, 137.9, 135.1, 133.5, 131.3, 130.8, 129.6, 129.4, 129.0, 125.4, 124.7, 121.8, 118.1, 116.4, 112.9, 21.5, 20.4

Example 18

2-Chloro-4-(3-methoxy-phenylamino)-2'-methylbenzophenone (Compound 118)

General Procedure: 1
Starting compound II: 3-Bromoanisole
Starting compound III: 4-Amino-2-chloro-2'-methylbenzophenone
Solvent: 1,4-Dioxane
Base: NaO-t-Bu
Purification: Chromatography using EtOAc/pentane 1:9 as eluant $^{13}$C NMR (CDCl$_3$): δ196.5, 160.8, 147.5, 141.5, 139.1, 137.9, 135.0, 133.4, 131.3, 130.9, 130.4, 129.7, 129.4, 125.4, 116.8, 113.3, 113.1, 108.9, 106.7, 55.3, 20.5

Example 19

2-Chloro-4-(4-chloro-phenylamino)-2'-methylbenzophenone (Compound 119)

General Procedure: 1
Starting compound II: 1-Bromo-4-chlorobenzene
Starting compound III: 4-Amino-2-chloro-2'-methylbenzophenone
Solvent: 1,4-Dioxane Base: NaO-t-Bu
Purification: Chromatography using EtOAc/pentane 1:9 as eluant and then trituration in Et$_2$O/pentane 1:1
$^{13}$C NMR (CDCl$_3$): δ196.5, 147.3, 138.9, 138.0, 135.0, 133.4, 131.4, 131.0, 129.8, 129.7, 128.7, 125.4, 122.1, 122.0, 116.6, 113.2, 20.5

Example 20

2-Chloro-2'-methyl-4-(4-phenyl-phenylamino) benzophenone (Compound 120)

General Procedure: 1
Starting compound II: 4-Bromobiphenyl
Starting compound III: 4-Amino-2-chloro-2'-methylbenzophenone
Solvent: 1,4-Dioxane
Base: NaO-t-Bu
Purification: Chromatography using EtOAc/pentane 1:9 as eluant
$^{13}$C NMR (CDCl$_3$): δ196.5, 147.5, 140.4, 139.5, 139.1, 137.9, 136.6, 135.1, 133.5, 131.3, 130.9, 129.7, 129.4, 128.8, 128.2, 127.1, 126.7, 125.4, 121.0, 116.6, 113.2, 20.5

Example 21

4-(4-Bromo-phenylamino)-2-chloro-2'-methylbenzophenone (Compound 121)

General Procedure: 1
Starting compound II: 1-Iodo-4-bromobenzene
Starting compound III: 4-Amino-2-chloro-2'-methylbenzophenone
Solvent: 1,4-Dioxane
Base: NaO-t-Bu
Purification: Chromatography using EtOAc/pentane 1:9 as eluant
$^{13}$C NMR (CDCl$_3$): δ196.5, 147.1, 139.5, 138.9, 138.1, 135.0, 133.3, 132.6, 131.4, 131.0, 129.9, 129.8, 125.4, 122.3, 116.8, 116.0, 113.3, 20.5

Example 22

4-(4-Bromo-3-fluoro-phenylamino)-2-chloro-2'-methylbenzophenone (Compound 122)

General Procedure: 1
Starting compound II: 1-Iodo-4-bromo-3-fluorobenzene
Starting compound III: 4-Amino-2-chloro-2'-methylbenzophenone
Solvent: 1,4-Dioxane
Base: NaO-t-Bu
Purification: Chromatography using EtOAc/pentane 1:9 as eluant
$^{13}$C NMR (CDCl$_3$): δ196.5, 159.6, 145.9, 141.7, 138.6, 138.3, 134.8, 134.1, 133.1, 131.5, 131.2, 131.0, 130.0, 125.5, 117.8, 116.5, 114.2, 107.7, 101.5, 20.6

Example 23

4-(2-Bromo-phenylamino)-2-chloro-2'-methylbenzophenone (Compound 123)

General Procedure: 1
Starting compound II: 1-Iodo-2-bromobenzene
Starting compound III: 4-Amino-2-chloro-2'-methylbenzophenone
Solvent: 1,4-Dioxane
Base: NaO-t-Bu
Purification: Chromatography using EtOAc/pentane 1:9 as eluant
$^{13}$C NMR (CDCl$_3$): δ196.4, 146.2, 138.7, 138.2, 134.7, 133.4, 133.1, 131.4, 131.1, 130.9, 130.0, 128.3, 125.4, 124.0, 119.8, 118.0, 115.3, 114.6, 20.6

Example 24

2-Chloro-4-(4-chloro-2-methyl-phenylamino)-2'-methylbenzophenone (Compound 124)

General Procedure: 1
Starting compound II: 2-Bromo-5-chlorotoluene
Starting compound III: 4-Amino-2-chloro-2'-methylbenzophenone
Solvent: 1,4-Dioxane
Base: NaO-t-Bu
Purification: Chromatography using EtOAc/pentane 1:9 as eluant
$^{13}$C NMR (CDCl$_3$): δ196.5, 148.5, 139.1, 137.9, 136.9, 135.1, 134.2, 133.5, 131.3, 131.2, 130.8, 130.3, 129.7, 129.0, 127.1, 125.4, 124.9, 116.0, 112.4, 20.4, 17.8

Example 25

2-Chloro-4-(4-chloro-3-fluoro-phenylamino)-2'-methylbenzophenone (Compound 125)

General Procedure: 1
Starting compound II: 1-Bromo-4-chloro-3-fluorobenzene
Starting compound III: 4-Amino-2-chloro-2'-methylbenzophenone
Solvent: 1,4-Dioxane
Base: NaO-t-Bu
Purification: Chromatography using EtOAc/pentane 1:9 as eluant
$^{13}$C NMR (CDCl$_3$): δ196.6, 158.6, 146.1, 140.9, 138.6, 138.2, 134.8, 133.1, 131.5, 131.2, 130.8, 130.0, 125.5, 117.6, 116.2, 114.0, 108.0, 20.6

Example 26

2-Chloro-4-(3-fluoro-phenylamino)-2'-methylbenzophenone (Compound 126)

General Procedure: 1
Starting compound II: 1-Bromo-3-fluorobenzene
Starting compound III: 4-Amino-2-chloro-2'-methylbenzophenone
Solvent: 1,4-Dioxane
Base: NaO-t-Bu
Purification: Chromatography using EtOAc/pentane 1:9 as eluant
$^{13}$C NMR (CDCl$_3$): δ196.6, 163.6, 146.6, 142.3, 138.8, 138.1, 134.9, 133.2, 131.4, 131.1, 130.8, 130.3, 129.9, 125.4, 117.4, 115.5, 113.8, 110.0, 107.0, 20.5

Example 27

2-Chloro-4-(3,5-difluoro-phenylamino)-2'-methylbenzophenone (Compound 127)

General Procedure: 1
Starting compound II: 1-Bromo-3,5-difluorobenzene
Starting compound III: 4-Amino-2-chloro-2'-methylbenzophenone
Solvent: 1,4-Dioxane
Base: NaO-t-Bu
Purification: Chromatography using EtOAc/pentane 1:9 as eluant
$^{13}$C NMR (CDCl$_3$): δ196.6, 164.0, 163.8, 145.4, 143.5, 138.4, 134.6, 132.9, 131.5, 131.4, 130.1, 125.5, 118.5, 114.9, 101.7, 101.7, 97.9, 20.6

Example 28

4-(3-Bromo-phenylamino)-2-chloro-2'-methylbenzophenone (Compound 128)

General Procedure: 1
Starting compound II: 1-Iodo-3-bromobenzene

Starting compound III: 4-Amino-2-chloro-2'-methylbenzophenone
Solvent: 1,4-Dioxane
Base: NaO-t-Bu
Purification: Chromatography using EtOAc/pentane 1:9 as eluant
$^{13}$C NMR (CDCl$_3$): δ196.5, 146.6, 142.0, 138.8, 138.1, 134.9, 133.3, 131.4, 131.1, 130.9, 130.3, 129.9, 126.3, 125.4, 123.2, 123.1, 118.7, 117.3, 113.7, 20.5

Example 29

2-Chloro-4-(3,4-difluoro-phenylamino)-2'-methylbenzophenone (Compound 129)
General Procedure: 1
Starting compound II: 1-Bromo-3,4-difluorobenzene
Starting compound III: 4-Amino-2-chloro-2'-methylbenzophenone
Solvent: 1,4-Dioxane
Base: NaO-t-Bu
Purification: Chromatography using CH$_2$Cl$_2$/pentane 2:1 as eluant
$^{13}$C NMR (CDCl$_3$): δ196.5, 147.2, 138.8, 138.1, 135.0, 133.3, 131.4, 131.1, 130.1, 129.9, 125.4, 118.2, 117.9, 117.1, 116.6, 113.1, 110.6, 20.5

Example 30

2-Chloro-4-(5-fluoro-2-methyl-phenylamino)-2'-methylbenzophenone (Compound 130)
General Procedure: 1
Starting compound II: 2-Bromo-4-fluorotoluene
Starting compound III: 4-Amino-2-chloro-2'-methylbenzophenone
Solvent: 1,4-Dioxane
Base: NaO-t-Bu
Purification: Chromatography using Et$_2$O/pentane 1:4 as eluant
$^{13}$C NMR (CDCl$_3$): δ196.5, 161.6, 147.6, 139.7, 139.0, 138.0, 135.0, 133.4, 132.1, 131.3, 131.0, 129.8, 129.7, 126.2, 125.4, 116.9, 113.2, 111.1, 108.8, 20.5, 17.2

Example 31

2-Chloro-4-(3-fluoro-2-methyl-phenylamino)-2'-methylbenzophenone (Compound 131)
General Procedure: 1
Starting compound II: 2-Bromo-6-fluorotoluene
Starting compound III: 4-Amino-2-chloro-2'-methylbenzophenone
Solvent: 1,4-Dioxane
Base: NaO-t-Bu
Purification: Chromatography using Et$_2$O/pentane 1:2 as eluant
$^{13}$C NMR (CDCl$_3$): δ196.5, 162.0, 148.3, 140.1, 139.1, 138.0, 135.0, 133.4, 131.3, 130.9, 129.7, 129.3, 127.2, 125.4, 119.3, 118.6, 116.4, 112.8, 111.7, 20.5, 9.6

Example 32

Ethyl 2-[[3-chloro-4-(2-methylbenzoyl)]phenylamino]benzoate (Compound 132)
General Procedure: 1
Starting compound II: Ethyl 2-bromobenzoate
Starting compound III:4-Amino-2-chloro-2'-methylbenzophenone
Solvent: Toluene
Base: Cs$_2$CO$_3$
Purification: Chromatography using EtOAc/pentane 1:50 as eluant
$^{13}$C NMR (CDCl$_3$): δ196.5, 168.3, 145.1, 144.9, 138.6, 138.4, 134.4, 134.0, 132.7, 131.8, 131.5, 131.2, 130.1, 125.4, 120.4, 119.6, 117.0, 116.0, 114.8, 61.1, 20.6, 14.3

Example 33

2-Chloro-3'-fluoro4-(4-fluoro-2-methyl-phenylamino)-2'-methylbenzophenone (Compound 133)
General Procedure: 1
Starting compound II: 2-Bromo-5-fluorotoluene
Starting compound III: 4-Amino-2-chloro-3'-fluoro-2'-methylbenzophenone
Solvent: Toluene
Base: Cs$_2$CO$_3$
Purification: Chromatography using EtOAc/pentane 1:9 as eluant
$^{13}$C NMR (CDCl$_3$): δ195.0, 161.5, 160.7, 150.1, 142.1, 136.5, 135.7, 134.1, 133.6, 127.4, 126.5, 124.5, 124.5, 117.9, 117.2, 115.2, 113.9, 111.5, 18.1, 11.5

Example 34

2-[[3-Chloro-4-(2-methylbenzoyl)]phenylamino]benzoic acid (Compound 134)

A solution of 50 mg Ethyl 2-[[3-chloro-4-(2-methylbenzoyl)]phenylamino]benzoate (Compound 132) in methanol (2.0 ml) was added aqueous NaOH (2N, 0.5 ml) and then refluxed for 1 h. The reaction mixture was made slightly acidic with aqueous HCl (1N) and then extracted with EtOAc (3*10 ml). The organic phase was washed with water, brine, then dried (MgSO$_4$), filtered, and concentrated in vacuo to afford the pure title compound.
$^{13}$C NMR (CDCl$_3$): δ196.6, 173.2, 146.0, 144.5, 138.6, 138.3, 135.3, 134.3, 132.9, 132.6, 132.5, 131.6, 131.4, 130.3, 125.5, 121.3, 119.7, 117.8, 115.8, 112.9, 20.7

Example 35

2-Chloro-4-(4-fluoro-2-methyl-N-methyl-phenylamino)-2'-methylbenzophenone (Compound 135)

A solution of 2-chloro-4-(4-fluoro-2-methyl-phenylamino)-2'-methylbenzophenone (Compound 116) (105 mg) in N-methyl-2-pyrolidinone (2.0 ml) was added sodium hydride (14 mg) in one portion under stirring. After 10 min at 0° C. methyl iodide (47 mg) was added and the reaction mixture was stirred for 4 hours at room temperature followed by 18 hours at 100° C. The reaction mixture was poured into water and extracted with EtOAc. The organic phases were separated, dried (MgSO$_4$), filtered and concentrated in vacuo. The residue was purified by chromatography using a mixture of diethylether/pentane 1:4 as eluant to yield the title compound.
$^{13}$C NMR (CDCl$_3$): δ196.2, 161.2, 151.7, 140.3, 139.5, 138.7, 137.2, 135.1, 133.5, 130.8, 130.2, 129.7, 129.0, 125.8, 125.0, 118.0, 114.5, 113.3, 109.6, 38.9, 20.0, 17.5

Example 36

4-(4-Bromo-2-methyl-phenylamino)-2-chloro-2'-methylbenzophenone (Compound 136)
General Procedure: 1
Starting compound II: 5-Bromo-2-iodotoluene
Starting compound III: 4-Amino-2-chloro-2'-methylbenzophenone Solvent: Toluene
Base: Cs$_2$CO$_3$
Purification: Chromatography using Et$_2$O/pentane 1:3 followed by 1:2 as eluant
$^{13}$C NMR (CDCl$_3$): δ196.6, 148.5, 139.1, 137.8, 137.5, 135.1, 134.5, 134.0, 133.6, 131.2, 130.8, 130.0, 129.6, 128.7, 125.4, 125.1, 117.9, 116.0, 112.4, 20.4, 17.8

Example 37

4-(4-Bromo-2-chloro-phenylamino)-2-chloro-2'-methylbenzophenone (Compound 137)

General Procedure: 1
Starting compound II: 4-bromo-2-chloro-1-iodobenzene
Starting compound III: 4-Amino-2-chloro-2'-methylbenzophenone
Solvent: 1,4-Dioxane
Base: Cs$_2$CO$_3$
Purification: Chromatography using EtOAc/pentane 1:9 as eluant
$^{13}$C NMR (CDCl$_3$): δ196.4, 145.3, 138.4, 138.4, 137.0, 134.6, 132.9, 132.6, 131.6, 131.5, 131.3, 130.7, 130.1, 125.4, 125.0, 120.0, 118.5, 115.1, 114.4, 20.6

Example 38

4-(4-Bromo-2-methyl-phenylamino)-2-chloro-4'-methoxy-2'-methylbenzophenone (Compound 138)

General Procedure: 1
Starting compound II: 5-Bromo-2-iodotoluene
Starting compound III: 4-Amino-2-chloro-4'-methoxy-2'-methylbenzophenone
Solvent: Toluene
Base: Cs$_2$CO$_3$
Purification: Chromatography using EtOAc/pentane 1:4 as eluant
$^{13}$C NMR (CDCl$_3$): δ195.5, 161.9, 147.5, 141.9, 137.8, 134.2, 134.0, 133.9, 133.6, 132.4, 131.0, 130.5, 130.0, 124.4, 117.5, 117.1, 116.1, 112.9, 110.4, 55.3, 21.5, 17.8

Example 39

4-(4-Bromo-2-methyl-phenylamino)-2,4'-dichloro-2'-methylbenzophenone (Compound 139)

General Procedure: 1
Starting compound II: 5-Bromo-2-iodotoluene
Starting compound III: 4-Amino-2,4'-dichloro-2'-methylbenzophenone
Solvent: Toluene
Base: Cs$_2$CO$_3$
Purification: Chromatography using EtOAc/pentane 1:3 as eluant
$^{13}$C NMR (CDCl$_3$): δ195.3, 148.6, 140.0, 137.6, 137.3, 136.7, 135.1, 134.5, 134.1, 133.4, 131.3, 131.0, 130.1, 128.6, 125.6, 125.1, 118.1, 116.0, 112.6, 20.3, 17.8

Example 40

4-(4-Bromo-2-methyl-phenylamino)-2-chloro-4'-fluoro-2'-methylbenzophenone (Compound 140)

General Procedure: 1
Starting compound II: 5-Bromo-2-iodotoluene
Starting compound III: 4-Amino-2-chloro-4'-fluoro-2'-methylbenzophenone
Solvent: Toluene
Base: Cs$_2$CO$_3$
Purification: Chromatography using EtOAc/pentane 1:6 as eluant
$^{13}$C NMR (CDCl$_3$): δ195.3, 164.0, 148.4, 141.7, 137.4, 135.2, 134.9, 134.4, 134.1, 133.2, 132.4, 130.1, 129.1, 125.0, 118.2, 118.0, 116.0, 112.7, 112.3, 20.7, 17.8

Example 41

4-(4-Bromo-2-methyl-phenylamino)-2-fluoro-2'-methylbenzophenone (Compound 141)

General Procedure: 1
Starting compound II: 5-Bromo-2-iodotoluene
Starting compound III: 4-Amino-2-fluoro-2'-methylbenzophenone
Solvent: Toluene
Base: Cs$_2$CO$_3$
Purification: Chromatography using EtOAc/pentane 1:6 as eluant
$^{13}$C NMR (CDCl$_3$): δ194.2, 163.7, 151.0, 140.4, 137.1, 136.3, 134.9, 134.1, 133.9, 130.9, 130.1, 128.1, 125.7, 125.3, 118.5, 117.8, 110.2, 101.1, 19.9, 17.7

Example 42

4-(4-Bromo-2-methyl-phenylamino)-2-chloro-2',5'-dimethyl-benzophenone (Compound 142)

General Procedure: 1
Starting compound II: 5-Bromo-2-iodotoluene
Starting compound III: 4-Amino-2-chloro-2',5'-dimethyl-benzophenone
Solvent: Toluene
Base: Cs$_2$CO$_3$
Purification: Chromatography using EtOAc/pentane 1:8 as eluant
$^{13}$C NMR (CDCl$_3$): δ196.6, 148.2, 139.0, 137.5, 135.1, 134.9, 134.7, 134.2, 134.1, 133.5, 131.6, 131.2, 130.1, 129.2, 124.8, 117.8, 116.2, 112.6, 20.8, 19.9, 17.8

Example 43

2-Chloro-4-(4-cyano-2-methyl-phenylamino)-2'-methylbenzophenone (Compound 143)

General Procedure: 1
Starting compound II: 4-Bromo-3-methylbenzonitrile
Starting compound III: 4-Amino-2-chloro-2'-methylbenzophenone
Solvent: Toluene
Base: Cs$_2$CO$_3$
Purification: Chromatography using EtOAc/pentane 1:3 as eluant
$^{13}$C NMR (CDCl$_3$): δ196.4, 145.0, 143.8, 138.5, 138.2, 134.8, 134.5, 132.8, 132.2, 131.6, 131.4, 131.4, 130.2, 128.1, 125.5, 119.5, 119.2, 117.4, 116.0, 105.1, 20.7, 17.7

Example 44

4-(4-Bromo-2-methyl-N-ethyl-phenylamino)-2-chloro-2'-methylbenzophenone (Compound 144)

A solution of 4-(4-bromo-2-methyl-phenylamino)-2-chloro-2'-methylbenzophenone (Compound 136)(110 mg) in dry tetrahydrofurane (2.0 ml was added sodium hydride (19 mg) in one portion under stirring. After 10 min at room temperature ethyl iodide (124 mg ) was added and the reaction mixture was stirred for 18 hours under reflux, then poured into water and extracted with EtOAc. The organic phases were separated, dried (MgSO$_4$), filtered and concentrated in vacuo. The residue was purified by chromatography using a mixture of EtOAc/pentane 1:8 as eluant to yield the title compound as an oil.
$^{13}$C NMR (CDCl$_3$): δ196.3, 150.8, 142.0, 139.7, 139.2, 137.4, 135.5, 134.7, 133.9, 131.1, 131.0, 130.4, 129.2, 126.0, 125.2, 121.2, 113.7, 109.9, 46.0, 20.2, 17.7, 12.4

Example 45

2-Chloro-4-(4-bromo-2-methyl-phenylamino)-4'-ethoxy-2'-methylbenzophenone (Compound 145)

General Procedure: 1
Starting compound II: 5-Bromo-2-iodotoluene
Starting compound III: 4-Amino-2-chloro-4'-ethoxy-2'-methylbenzophenone
Solvent: Toluene
Base: $Cs_2CO_3$
Purification: Chromatography using EtOAc/pentane 1:4 as eluant
$^{13}C$ NMR ($CDCl_3$): δ195.5, 161.4, 147.5, 142.0, 137.9, 134.2, 134.0, 133.8, 133.7, 132.4, 130.7, 130.6, 130.0, 124.4, 117.6, 117.4, 116.1, 113.0, 110.8, 63.5, 21.5, 17.8, 14.7

Example 46

2,3'-Dichloro-4-(4-bromo-2-methyl-phenylamino)-2'-methylbenzophenone (Compound 146)

General Procedure: 1
Starting compound II: 5-Bromo-2-iodotoluene
Starting compound III: 4-Amino-2,3'-dichloro-2'-methylbenzophenone
Solvent: Toluene
Base: $Cs_2CO_3$
Purification: Chromatography using acetone/toluene 1:99 as eluant
$^{13}C$ NMR ($CDCl_3$): δ195.2, 149.1, 142.1, 137.1, 135.9, 135.8, 134.9, 134.7, 134.3, 134.1, 131.1, 130.1, 127.7, 126.8, 126.4, 125.5, 118.4, 116.1, 112.3, 17.8, 17.1

Example 47

| Tablet containing compound 102 | |
| --- | --- |
| Compound 102 (active substance) | 50 mg |
| Lactose | 125 mg |
| Starch | 12 mg |
| Methyl cellulose | 2 mg |
| Sodium carboxymethyl cellulose | 10 mg |
| Magnesium stearate | 1 mg |

The active substance, lactose and starch are mixed to a homogeneous state in a suitable mixer and moistened with a 5 percent aqueous solution of methyl cellulose 15 cps. The mixing is continued until granules are formed. If necessary, the wet granulation is passed through a suitable screen and dried to a water content of less than 1% in a suitable drier, e.g. fluid bed or drying oven. The dried granules are passed through a 1 mm screen and mixed to a homogeneous state with sodium carboxymethyl cellulose. Magnesium stearate is added, and the mixing is continued for a short period of time. Tablets with a weight of 200 mg are produced from the granulation by means of a suitable tabletting machine.

Example 48

Formulation for Injection Containing Compound 102

| Compound 102 (active substance) | 1% |
| --- | --- |
| Sodium chloride | q.s. |
| Ethanol | 10% |
| Water for injection to make | 100% |

The active substance is dissolved in ethanol (10%) then water for injection made isotonic with sodium chloride is added to make 100%. The mixture is filled into ampoules and sterilized.

Example 49

Cream Formulation Containing Compound 102

Compound 102 (10 g) was dissolved in Octyldodecyl myristate (250 g) to form Part A. Methylparaben (1 g) and propylparaben (0.2 g) were dissolved in phenoxyethanol (6 g) and mixed with a 0.025 M Phosphate buffer pH=7.5 (632,8 g) to form Part B. Cetostearyl alcohol (50 g) and ARLACEL 165® (50 g) was melted in a vessel at 70° to 80° C. Part A was added and heated to 60–70° C. The aqueous phase was likewise heated to 60–70° C. and slowly added to the melted oil phase under high speed stirring. The homogenized components were cooled to room temperature.

What is claimed is:

1. A compound of the general formula VII

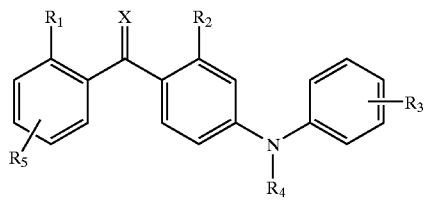

wherein
$R_1$ represents a substituent selected from the group consisting of halogen, hydroxy, mercapto, trifluoromethyl, amino, $(C_1-C_3)$alkyl, $(C_2-C_3)$olefinic group, $(C_1-C_3)$alkoxy, $(C_1-C_3)$alkylthio, $(C_1-C_6)$alkylamino, $(C_1-C_3)$alkoxycarbonyl, cyano, —$CONH_2$, phenyl, and nitro;

$R_2$ represents a substituent selected from the group consisting of halogen, hydroxy, mercapto, trifluoromethyl, amino, $(C_1-C_3)$alkyl, $(C_2-C_3)$olefinic group, $(C_1-C_3)$alkoxy, $(C_1-C_3)$alkylthio, $(C_1-C_6)$alkylamino, $(C_1-C_3)$alkoxycarbonyl, cyano, —$CONH_2$, phenyl, and nitro;

$R_3$ represents one or more, same or different substituents selected from the group consisting of hydrogen, halogen, hydroxy, mercapto, trifluoromethyl, cyano, carboxy, carbamoyl, $(C_1-C_{10})$alkyl, $(C_2-C_{10})$olefinic group, $(C_3-C_8)$monocyclic hydrocarbon group, $(C_1-C_{10})$alkoxy, $(C_1-C_{10})$alkylthio, $(C_1-C_{10})$alkoxycarbonyl, and phenyl;

$R_4$ represents hydrogen, $(C_1-C_6)$alkyl, $(C_2-C_6)$olefinic group, or $(C_3-C_6)$monocyclic hydrocarbon group;

$R_5$ represents one or more, same or different substituents selected from the group consisting of hydrogen and $R_1$;

X represents oxygen, sulphur, or N—OH;

and salts thereof with pharmaceutically acceptable acids, hydrates and solvates, with the proviso that when X represents oxygen then $R_1$, $R_2$ and $R_5$ together does not represent more than 8 fluorine substituents.

2. A compound according to claim 1 wherein $R_1$ represents a substituent selected from the group consisting of fluoro, chloro, bromo, hydroxy, trifluoromethyl, amino, $(C_1-C_2)$alkyl, $(C_2-C_3)$alkenyl, $(C_1-C_3)$alkoxy, $(C_1-C_3)$alkoxycarbonyl, cyano, and —$CONH_2$.

3. A compound according to claim 1 wherein $R_2$ represents a substituent selected from the group consisting of fluoro, chloro, bromo, hydroxy, trifluoromethyl, amino, $(C_1-C_3)$alkyl, $(C_2-C_3)$alkenyl, and $(C_1-C_3)$alkoxy.

4. A compound according to claim 1 wherein $R_3$ represents one or more, same or different substituents selected from the group consisting of hydrogen, fluoro, chloro, bromo, hydroxy, trifluoromethyl, $(C_1-C_6)$alkyl, $(C_2-C_6)$alkenyl, $(C_1-C_6)$alkoxy, $(C_1-C_6)$alkoxycarbonyl, cyano, carboxy, and —$CONH_2$.

5. A compound according to claim 1 wherein $R_4$ represents hydrogen, $(C_1-C_4)$alkyl, or $(C_2-C_4)$olefinic group.

6. A compound according to claim 1 wherein X represents oxygen or sulphur.

7. A compound according to claim 1 wherein $R_5$ represents one or more, same or different substituents selected from the group consisting of hydrogen, fluoro, chloro, bromo, hydroxy, trifluoromethyl, amino, $(C_1-C_2)$alkyl, $(C_2-C_3)$ alkenyl, $(C_1-C_3)$alkoxy, $(C_1-C_3)$alkoxycarbonyl, cyano, and —$CONH_2$.

8. A compound according to claim 1 wherein $R_1$ represents a substituent selected from the group consisting of fluoro, chloro, bromo, hydroxy, methyl, and methoxy.

9. A compound according to claim 1 wherein $R_2$ represents a substituent selected from the group consisting of fluoro, chloro, bromo, hydroxy, methyl, and methoxy.

10. A compound according to claim 1 wherein $R_3$ represents one or more, same or different substituents selected from the group consisting of hydrogen, fluoro, chloro, bromo, hydroxy, methyl, methoxy, cyano, and carboxy.

11. A compound according to claim 1 wherein $R_4$ represents hydrogen, methyl, or ethyl.

12. A compound according to claim 1 wherein $R_5$ represents one or more, same or different substituents selected from the group consisting of hydrogen, fluoro, chloro, bromo, hydroxy, trifluoromethyl, methyl, ethyl, and methoxy.

13. A compound according to claim 1 wherein X represents oxygen.

14. A compound according to claim 1, wherein at least one of $R_1$, $R_2$, $R_3$, and $R_5$ represents a phenyl group said group is optionally substituted with a substituent selected from the group consisting of hydroxy, amino, nitro, cyano, halogen, methyl, and methoxy.

15. A compound according to claim 1, wherein said halogen is selected from the group consisting of fluoro, chloro, and bromo.

16. A compound according to claim 1 wherein $R_2$ represents a halogen atom.

17. A compound according to claim 1 wherein $R_2$ represents chlorine.

18. A compound according to claim 1 selected from the group consisting of 2-[[3-Chloro-4-(2-methylbenzoyl)]phenylamino]benzonitrile (Compound 101), 2-Chloro-2'-methyl-4-(2-methyl-phenylamino)benzophenone (Compound 102),
2-Chloro-2'-methyl-4-(phenylamino)benzophenone (Compound 103),
2-Chloro-4-(2-methoxy-phenylamino)-2'-methylbenzophenone (Compound 104),
2-Chloro-4-(2-fluoro-phenylamino)-2'-methylbenzophenone (Compound 105),
2-Chloro-4-(2-chloro-phenylamino)-2'-methylbenzophenone (Compound 106),
4-(2-tert-Butoxy-phenylamino)-2-chloro-2'-methylbenzophenone (Compound 107),
2-Chloro-4-(2-hydroxy-phenylamino)-2'-methylbenzophenone (Compound 108),
2-Chloro-4-(3-chloro-phenylamino)-2'-methylbenzophenone (Compound 109),
2-Chloro-4-(2-[1,1,1-trifluoromethyl]-phenylamino)-2'-methylbenzophenone (Compound 110), 4-(4-Bromo-2,5-difluoro-phenylamino)-2-chloro-2'-methylbenzophenone (Compound 111),
2-Chloro-4-(2-ethyl-phenylamino)-2'-methylbenzophenone (Compound 112),
2-Chloro-4-(3-[1,1,1-trifluoromethyl]phenylamino)-2'-methylbenzophenone (Compound 113),
2-Chloro-2'-methyl-4-(2-phenyl-phenylamino)benzophenone (Compound 114),
2-Chloro-2'-methyl-4-(3-phenyl-phenylamino)benzophenone (Compound 115),
2-Chloro-4-(4-fluoro-2-methyl-phenylamino)-2'-methylbenzophenone (Compound 116),
2-Chloro-2'-methyl-4-(3-methyl-phenylamino)benzophenone (Compound 117),
2-Chloro-4-(3-methoxy-phenylamino)-2'-methylbenzophenone (Compound 118),
2-Chloro-4-(4-chloro-phenylamino)-2'-methylbenzophenone (Compound 119),
2-Chloro-2'-methyl-4-(4-phenyl-phenylamino)benzophenone (Compound 120),
4-(4-Bromo-phenylamino)-2-chloro-2'-methylbenzophenone (Compound 121),
4-(4-Bromo-3-fluoro-phenylamino)-2-chloro-2'-methylbenzophenone (Compound 122),
4-(2-Bromo-phenylamino)-2-chloro-2'-methylbenzophenone (Compound 123),
2-Chloro-4-(4-chloro-2-methyl-phenylamino)-2'-methylbenzophenone (Compound 124),
2-Chloro-4-(4-chloro-3-fluoro-phenylamino)-2'-methylbenzophenone (Compound 125),
2-Chloro-4-(3-fluoro-phenylamino)-2'-methylbenzophenone (Compound 126),
2-Chloro-4-(3,5-difluoro-phenylamino)-2'-methylbenzophenone (Compound 127),
4-(3-Bromo-phenylamino)-2-chloro-2'-methylbenzophenone (Compound 128),
2-Chloro-4-(3,4-difluoro-phenylamino)-2'-methylbenzophenone (Compound 129),
2-Chloro-4-(5-fluoro-2-methyl-phenylamino)-2'-methylbenzophenone (Compound 130),
2-Chloro-4-(3-fluoro-2-methyl-phenylamino)-2'-methylbenzophenone (Compound 131),
Ethyl 2-[[3-chloro-4-(2-methylbenzoyl)]phenylamino] benzoate (Compound 132),
2-Chloro-3'-fluoro-4-(4-fluoro-2-methyl-phenylamino)-2'-methylbenzophenone (Compound 133),
2-[[3-Chloro-4-(2-methylbenzoyl)]phenylamino]benzoic acid (Compound 134),
2-Chloro-4-(4-fluoro-2-methyl-N-methyl-phenylamino)-2'-methylbenzophenone (Compound 135),
4-(4-Bromo-2-methyl-phenylamino)-2-chloro-2'-methylbenzophenone (Compound 136),
4-(4-Bromo-2-chloro-phenylamino)-2-chloro-2'-methylbenzophenone (Compound 137),
4-(4-Bromo-2-methyl-phenylamino)-2-chloro-4'-methoxy-2'-methylbenzophenone (Compound 138),
4-(4-Bromo-2-methyl-phenylamino)-2,4'-dichloro-2'-methylbenzophenone (Compound 139),
4-(4-Bromo-2-methyl-phenylamino)-2-chloro-4'-fluoro-2'-methylbenzophenone (Compound 140),
4-(4-Bromo-2-methyl-phenylamino)-2-fluoro-2'-methylbenzophenone (Compound 141),
4-(4-Bromo-2-methyl-phenylamino)-2-chloro-2',5'-dimethyl-benzophenone (Compound 142),
2-Chloro-4-(4-cyano-2-methyl-phenylamino)-2'-methylbenzophenone (Compound 143),
4-(4-Bromo-2-methyl-N-ethyl-phenylamino)-2-chloro-2'-methylbenzophenone (Compound 144),
2-Chloro-4-(4-bromo-2-methyl-phenylamino)-4'-ethoxy-2'-methylbenzophenone (Compound 145),
2,3'-Dichloro-4-(4-bromo-2-methyl-phenylamino)-2'-methylbenzophenone (Compound 146), and salts thereof with pharmaceutically acceptable acids, hydrates and solvates.

19. A compound of claim 1, wherein the compound is in the form of a salt, which is formed with a pharmaceutically acceptable inorganic or organic acid selected from the group consisting of hydrochloric acid, hydrobromic acid, hydroiodic acid, phosphoric acid, sulphuric acid, nitric acid, p-toluenesulphonic acid, methanesulphonic acid, formic acid, acetic acid, propionic acid, citric acid, tartaric acid, succinic acid, benzoic acid, and maleic acid.

20. A pharmaceutical composition containing as an active ingredient a compound according to claim 1 together with a pharmaceutically acceptable carrier and optionally together with a second active ingredient optionally selected from the group consisting of glucocorticoids, vitamin D analogues, anti-histamines, platelet activating factor (PAF) antagonists, anticolinergic agents, methyl xanthines, β-adrenergic agents, COX-2 inhibitors, salicylates, indomethacin, flufenamate, naproxen, timegadine, gold salts, penicillamine, serum cholesterol-reducing agents, retinoids, zinc salts, and salicylazosulfapyridin (Salazopyrin).

21. A method for the treatment and/or prophylaxis of a disease or disorder comprising administering to a patient suffering from said disease or disorder an effective amount of the composition of claim 20 wherein said disease or disorder is selected from the group consisting of asthma, allergy, arthritis, including rheumatoid arthritis and spondylo arthritis, gout, atherosclerosis, chronic inflammatory bowel disease (Crohn's disease), proliferative and inflammatory skin disorders, such as psoriasis, atopic dermatitis, uveitis, septic shock, AIDS, osteoporosis and acne.

22. A compound of the general formula Ia or Ib

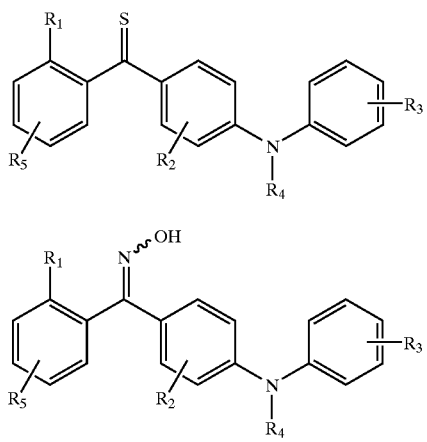

wherein $R_1$, $R_2$, $R_3$, $R_4$, and $R_5$ have the meanings specified for formula VII, and salts thereof with pharmaceutically acceptable acids, hydrates and solvates.

23. A compound of formulae 1a or 1b of claim 22, wherein the compound is in the form of a salt, which is formed with a pharmaceutically acceptable inorganic or organic acid selected from the group consisting of hydrochloric acid, hydrobromic acid, hydroiodic acid, phosphoric acid, sulphuric acid, nitric acid, p-toluenesulphonic acid, methanesulphonic acid, formic acid, acetic acid, propionic acid, citric acid, tartaric acid, succinic acid, benzoic acid, and maleic acid.

24. A pharmaceutical composition containing as an active ingredient a compound according to claim 22 together with a pharmaceutically acceptable carrier and optionally together with a second active ingredient optionally selected from the group consisting of glucocorticoids, vitamin D analogues, anti-histamines, platelet activating factor (PAF) antagonists, anticolinergic agents, methyl xanthines, β-adrenergic agents, COX-2 inhibitors, salicylates, indomethacin, flufenamate, naproxen, timegadine, gold salts, penicillamine, serum cholesterol-reducing agents, retinoids, zinc salts, and salicylazosulfapyridin (Salazopyrin).

25. A pharmaceutical composition according to claim 20, 23 or 24 wherein the active ingredient comprises from 0.1% to 100% by weight of the composition.

26. A pharmaceutical preparation according to claim 20, 23 or 24 in unit dosage form containing between 0.07 mg and 1 g of the active ingredient.

27. A method for the treatment and/or prophylaxis of a disease or disorder comprising administering to a patient suffering from said disease or disorder an effective amount of the composition of claim 24 wherein said disease or disorder is selected from the group consisting of asthma, allergy, arthritis, including rheumatoid arthritis and spondylo arthritis, gout, atherosclerosis, chronic inflammatory bowel disease (Crohn's disease), proliferative and inflammatory skin disorders, such as psoriasis, atopic dermatitis, uveitis, septic shock, AIDS, osteoporosis and acne.

28. A method of treatment according to claim 21 or 27, comprising administering to said patient in need of systemic treatment a suitable dose of from 0.1 to 200 mg/kg bodyweight one or more times daily.

29. A method for the treatment according to claim 21 or 27 comprising adjusting to said patient in need of systematic treatment a suitable dose of from 0.2 to 50 mg/kg body weight one or more times daily.

30. A compound of formula Ia selected from the group consisting of

2-[[3-Chloro-4-(2-methyl(thiobenzoyl))]phenylamino] benzonitrile (Compound 301),
2-Chloro-2'-methyl-4-(2-methyl-phenylamino) (thiobenzophenone) (Compound 302),
2-Chloro-2'-methyl-4-(phenylamino)(thiobenzophenone) (Compound 303),
2-Chloro-4-(2-methoxy-phenylamino)-2'-methyl (thiobenzophenone) (Compound 304),
2-Chloro-4-(2-fluoro-phenylamino)-2'-methyl (thiobenzophenone) (Compound 305),
2-Chloro-4-(2-chloro-phenylamino)-2'-methyl (thiobenzophenone) (Compound 306),
4-(2-tert-Butoxy-phenylamino)-2-chloro-2'-methyl (thiobenzophenone) (Compound 307),
2-Chloro-4-(2-hydroxy-phenylamino)-2'-methyl (thiobenzophenone) (Compound 308),
2-Chloro-4-(3-chloro-phenylamino)-2'-methyl (thiobenzophenone) (Compound 309),
2-Chloro-4-(2-[1,1,1-trifluoromethyl]-phenylamino)-2'-methyl(thiobenzophenone) (Compound 310),
4-(4-Bromo-2,5-difluoro-phenylamino)-2-chloro-2'-methyl (thiobenzophenone) (Compound 311),
2-Chloro-4-(2-ethyl-phenylamino)-2'-methyl (thiobenzophenone) (Compound 312),
2-Chloro-4-(3-[1,1,1-trifluoromethyl]phenylamino)-2'-methyl(thiobenzophenone) (Compound 313),
2-Chloro-2'-methyl-4-(2-phenyl-phenylamino) (thiobenzophenone) (Compound 314),
2-Chloro-2'-methyl-4-(3-phenyl-phenylamino) (thiobenzophenone) (Compound 315), 2-Chloro-4-(4-fluoro-2-methyl-phenylamino)-2'-methyl (thiobenzophenone) (Compound 316),
2-Chloro-2'-methyl-4-(3-methyl-phenylamino) (thiobenzophenone) (Compound 317),
2-Chloro-4-(3-methoxy-phenylamino)-2'-methyl (thiobenzophenone) (Compound 318),
2-Chloro-4-(4-chloro-phenylamino)-2'-methyl (thiobenzophenone) (Compound 319),
2-Chloro-2'-methyl-4-(4-phenyl-phenylamino) (thiobenzophenone) (Compound 320),
4-(4-Bromo-phenylamino)-2-chloro-2'-methyl (thiobenzophenone) (Compound 321),
4-(4-Bromo-3-fluoro-phenylamino)-2-chloro-2'-methyl (thiobenzophenone) (Compound 322),
4-(2-Bromo-phenylamino)-2-chloro-2'-methyl (thiobenzophenone) (Compound 323),
2-Chloro-4-(4-chloro-2-methyl-phenylamino)-2'-methyl (thiobenzophenone) (Compound 324),
2-Chloro-4-(4-chloro-3-fluoro-phenylamino)-2'-methyl (thiobenzophenone) (Compound 325),
2-Chloro-4-(3-fluoro-phenylamino)-2'-methyl (thiobenzophenone) (Compound 326),
2-Chloro-4-(3,5-difluoro-phenylamino)-2'-methyl (thiobenzophenone) (Compound 327),
4-(3-Bromo-phenylamino)-2-chloro-2'-methyl (thiobenzophenone) (Compound 328),
2-Chloro-4-(3,4-difluoro-phenylamino)-2'-methyl (thiobenzophenone) (Compound 329),
2-Chloro-4-(5-fluoro-2-methyl-phenylamino)-2'-methyl (thiobenzophenone) (Compound 330),
2-Chloro-4-(3-fluoro-2-methyl-phenylamino)-2'-methyl (thiobenzophenone) (Compound 331),
Ethyl 2-[[3-chloro-4-(2-methyl(thiobenzoyl))]phenylamino] benzoate (Compound 332),
2-Chloro-3'-fluoro-4-(4-fluoro-2-methyl-phenylamino)-2'-methyl(thiobenzophenone) (Compound 333),
2-[[3-Chloro-4-(2-methyl(thiobenzoyl))]phenylamino] benzoic acid (Compound 334),
2-Chloro-4-(4-fluoro-2-methyl-N-methyl-phenylamino)-2'-methyl(thiobenzophenone) (Compound 335),
4-(4-Bromo-2-methyl-phenylamino)-2-chloro-2'-methyl (thiobenzophenone) (Compound 336),
4-(4-Bromo-2-chloro-phenylamino)-2-chloro-2'-methyl (thiobenzophenone) (Compound 337),
4-(4-Bromo-2-methyl-phenylamino)-2-chloro-4'-methoxy-2'-methyl(thiobenzophenone) (Compound 338),
4-(4-Bromo-2-methyl-phenylamino)-2,4'-dichloro-2'-methyl(thiobenzophenone) (Compound 339),
4-(4-Bromo-2-methyl-phenylamino)-2-chloro-4'-fluoro-2'-methyl(thiobenzophenone) (Compound 340),
4-(4-Bromo-2-methyl-phenylamino)-2-fluoro-2'-methyl (thiobenzophenone) (Compound 341),
4-(4-Bromo-2-methyl-phenylamino)-2-chloro-2',5'-dimethyl-(thiobenzophenone) (Compound 342),
2-Chloro-4-(4-cyano-2-methyl-phenylamino)-2'-methyl (thiobenzophenone) (Compound 343),
4-(4-Bromo-2-methyl-N-ethyl-phenylamino)-2-chloro-2'-methyl(thiobenzophenone) (Compound 344),
2-Chloro-4-(4-bromo-2-methyl-phenylamino)-4'-ethoxy-2'-methyl(thiobenzophenone) (Compound 345),
2,3'-Dichloro-4-(4-bromo-2-methyl-phenylamino)-2'-methyl(thiobenzophenone) (Compound 346), and salts thereof with pharmaceutically acceptable acids, hydrates and solvates.

31. A compound of formula Ib selected from the group consisting of

2-[[3-Chloro-4-[(hydroxyimino)(2-methylphenyl)methyl]] phenylamino]benzonitrile (Compound 401),
2-Chloro-2'-methyl-4-(2-methyl-phenylamino) benzophenone oxime (Compound 402),
2-Chloro-2'-methyl-4-(phenylamino)benzophenone oxime (Compound 403),
2-Chloro-4-(2-methoxy-phenylamino)-2'-methylbenzophenone oxime (Compound 404),
2-Chloro-4-(2-fluoro-phenylamino)-2'-methylbenzophenone oxime (Compound 405),
2-Chloro-4-(2-chloro-phenylamino)-2'-methylbenzophenone oxime (Compound 406),
4-(2-tert-Butyoxy-phenylamino)-2-chloro-2'-methylbenzophenone oxime (Compound 407),
2-Chloro-4-(2-hydroxy-phenylamino)-2'-methylbenzophenone oxime (Compound 408),
2-Chloro-4-(3-chloro-phenylamino)-2'-methylbenzophenone oxime (Compound 409),
2-Chloro-4-(2-[1,1,1-trifluoromethyl]-phenylamino)-2'-methylbenzophenone oxime (Compound 410),
4-(4-Bromo-2,5-difluoro-phenylamino)-2-chloro-2'-methylbenzophenone oxime (Compound 411),
2-Chloro-4-(2-ethyl-phenylamino)-2'-methylbenzophenone oxime (Compound 412),
2-Chloro-4-(3-[1,1,1-trifluoromethyl]phenylamino)-2'-methylbenzophenone oxime (Compound 413),
2-Chloro-2'-methyl-4-(2-phenyl-phenylamino) benzophenone oxime (Compound 414),
2-Chloro-2'-methyl-4-(3-phenyl-phenylamino) benzophenone oxime (Compound 415),
2-Chloro-4-(4-fluoro-2-methyl-phenylamino)-2'-methylbenzophenone oxime (Compound 416),
2-Chloro-2'-methyl-4-(3-methyl-phenylamino) benzophenone oxime (Compound 417),
2-Chloro-4-(3-methoxy-phenylamino)-2'-methylbenzophenone oxime (Compound 418),
2-Chloro-4-(4-chloro-phenylamino)-2'-methylbenzophenone oxime (Compound 419),
2-Chloro-2'-methyl-4-(4-phenyl-phenylamino) benzophenone oxime (Compound 420),
4-(4-Bromo-phenylamino)-2-chloro-2'-methylbenzophenone oxime(Compound 421),
4-(4-Bromo-3-fluoro-phenylamino)-2-chloro-2'-methylbenzophenone oxime (Compound 422),
4-(2-Bromo-phenylamino)-2-chloro-2'-methylbenzophenone oxime (Compound 423),
2-Chloro-4-(4-chloro-2-methyl-phenylamino)-2'-methylbenzophenone oxime (Compound 424),
2-Chloro-4-(4-chloro-3-fluoro-phenylamino)-2'-methylbenzophenone oxime (Compound 425),
2-Chloro-4-(3-fluoro-phenylamino)-2'-methylbenzophenone oxime (Compound 426),
2-Chloro-4-(3,5-difluoro-phenylamino)-2'-methylbenzophenone oxime (Compound 427),
4-(3-Bromo-phenylamino)-2-chloro-2'-methylbenzophenone oxime (Compound 428),
2-Chloro-4-(3,4-difluoro-phenylamino)-2'-methylbenzophenone oxime (Compound 429),
2-Chloro-4-(5-fluoro-2-methyl-phenylamino)-2'-methylbenzophenone oxime (Compound 430),
2-Chloro-4-(3-fluoro-2-methyl-phenylamino)-2'-methylbenzophenone oxime (Compound 431),
Ethyl 2-[[3-chloro-4-[(hydroxyimino)(2-methylphenyl) methyl]]phenylamino]benzoate (Compound 432),
2-Chloro-3'-fluoro-4-(4-fluoro-2-methyl-phenylamino)-2'-methylbenzophenone oxime (Compound 433), 2-[[3-Chloro-4-[(hydroxyimino)(2-methylphenyl)methyl]]phenylamino]benzoic acid (Compound 434), 2-Chloro-4-(4-fluoro-2-methyl-N-methyl-phenylamino)-2'-methylbenzophenone oxime (Compound 435), 4-(4-Bromo-2-methyl-phenylamino)-2-chloro-2'-methylbenzophenone oxime (Compound 436), 4-(4-Bromo-2-chloro-phenylamino)-2-chloro-2'-methylbenzophenone oxime (Compound 437), 4-(4-Bromo-2-methyl-phenylamino)-2-chloro-4'-methoxy-2'-methylbenzophenone oxime (Compound 438), 4-(4-Bromo-2-methyl-phenylamino)-2,4'-dichloro-2'-methylbenzophenone oxime (Compound 439), 4-(4-Bromo-2-methyl-phenylamino)-2-chloro-4'-fluoro-2'-methylbenzophenone oxime (Compound 440), 4-(4-Bromo-2-methyl-phenylamino)-2-fluoro-2'-methylbenzophenone oxime (Compound 441), 4-(4-Bromo-2-methyl-phenylamino)-2-chloro-2',5'-dimethyl-benzophenone oxime (Compound 442), 2-Chloro-4-(4-cyano-2-methyl-phenylamino)-2'-methylbenzophenone oxime (Compound 443), 4-(4-Bromo-2-methyl-N-ethyl-phenylamino)-2-chloro-2'-methylbenzophenone oxime (Compound 444), 2-Chloro-4-(4-bromo-2-methyl-phenylamino)-4'-ethoxy-2'-methylbenzophenone oxime (Compound 445), 2,3'-Dichloro-4-(4-bromo-2-methyl-phenylamino)-2'-methylbenzophenone oxime (Compound 446), and salts thereof with pharmaceutically acceptable acids, hydrates and solvates.

* * * * *